United States Patent
Pesaro et al.

(10) Patent No.: US 10,639,253 B2
(45) Date of Patent: May 5, 2020

(54) COMPOSITIONS

(71) Applicant: Symrise AG, Holzminden (DE)

(72) Inventors: Manuel Pesaro, Beverungen (DE); Benoit Join, Holzminden (DE); Arnold Machinek, Holzminden (DE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 14/946,163

(22) Filed: Nov. 19, 2015

(65) Prior Publication Data

US 2016/0143825 A1 May 26, 2016

(30) Foreign Application Priority Data

Nov. 21, 2014 (EP) .................................. 14194402

(51) Int. Cl.
| | | |
|---|---|---|
| *A61K 8/37* | (2006.01) | |
| *A61K 8/33* | (2006.01) | |
| *A61K 8/34* | (2006.01) | |
| *A61Q 11/00* | (2006.01) | |
| *A61Q 13/00* | (2006.01) | |
| *A61Q 15/00* | (2006.01) | |
| *A61Q 19/00* | (2006.01) | |
| *A61Q 19/08* | (2006.01) | |
| *A61Q 19/10* | (2006.01) | |
| *A61Q 5/02* | (2006.01) | |
| *A61Q 5/12* | (2006.01) | |
| *A61Q 9/02* | (2006.01) | |
| *A61Q 9/04* | (2006.01) | |
| *A61Q 17/00* | (2006.01) | |
| *A61Q 17/04* | (2006.01) | |

(52) U.S. Cl.
CPC .................. *A61K 8/37* (2013.01); *A61K 8/33* (2013.01); *A61K 8/34* (2013.01); *A61K 8/347* (2013.01); *A61Q 5/12* (2013.01); *A61Q 9/04* (2013.01); *A61Q 13/00* (2013.01); *A61Q 15/00* (2013.01); *A61Q 17/005* (2013.01); *A61Q 17/04* (2013.01); *A61Q 19/00* (2013.01); *A61Q 19/08* (2013.01); *A61K 2800/10* (2013.01); *A61Q 5/02* (2013.01); *A61Q 9/02* (2013.01); *A61Q 11/00* (2013.01); *A61Q 19/10* (2013.01)

(58) Field of Classification Search
CPC .......... A61K 8/37; A61K 8/42; A61K 8/4973; A61K 8/042; A61K 8/062; A61K 8/064; A61K 2800/77; A61Q 5/02; A61Q 5/12; A61Q 17/005; A61Q 19/10
See application file for complete search history.

(56) References Cited

U.S. PATENT DOCUMENTS

| | | | | |
|---|---|---|---|---|
| 4,507,319 | A | * | 3/1985 | Barratt .................. A61K 8/365 514/546 |
| 2006/0110415 | A1 | | 5/2006 | Gupta |
| 2007/0178128 | A1 | * | 8/2007 | Bessette ................ A01N 65/00 424/408 |
| 2008/0153757 | A1 | | 6/2008 | Beeson et al. |
| 2014/0010902 | A1 | | 1/2014 | Rockhill et al. |
| 2014/0031425 | A1 | | 1/2014 | Lopes |

FOREIGN PATENT DOCUMENTS

| | | |
|---|---|---|
| CN | 102 551 021 B | 5/2013 |
| JP | 2000-186001 A | 7/2000 |
| WO | 2007/071089 A1 | 6/2007 |
| WO | 2013/083405 A1 | 6/2013 |

OTHER PUBLICATIONS

Fernandez-Garcia et al, "Quantification of significant volatile components of pacharán," Z. Lebensrn, Unters. Forsch. A (1998), vol. 206, No. 6. pp. 414-416.
Friedman et al, "Antibacterial Activities of Phenolic Benzaldehydes and Benzoic Acids against Campylobacter jejuni, *Escherichia coli*, Listeria monocytogenes, and *Salmonella enterica*," Journal of Food Protection, vol. 66, No. 10, Oct. 1, 2003. pp. 1811-1821.

* cited by examiner

*Primary Examiner* — Lezah Roberts
(74) *Attorney, Agent, or Firm* — Dilworth & Barrese, LLP

(57) ABSTRACT

Suggested is a composition comprising
(a) at least one lactate ester and
(b1) at least one second compound selected from the group encompassing benzaldehyde derivatives, aromatic aldehydes and aromatic acids.

14 Claims, No Drawings

COMPOSITIONS

FIELD OF INVENTION

The present invention belongs to the area of flavours and fragrances and refers to new compositions comprising lactate esters, said compositions exhibiting antimicrobial activity.

STATE OF THE ART

In the cosmetics and pharmaceutical and in the foodstuffs industry there is a constant need for agents having antimicrobial properties, in particular for the preservation of products which are otherwise perishable (such as e.g. cosmetics, pharmaceutical products or foodstuffs), but also for direct cosmetic or therapeutic treatment of microorganisms which can have an adverse influence on the human or animal body. Reference may be made by way of example to microorganisms which can cause body odor, acne, mycoses or the like.

In the technical fields referred to a large number of antimicrobial active compounds are indeed already employed, but alternatives nevertheless continue to be sought, in order to be able to perform targeted specific treatments and/or reduce toxicological side effects. In this context, however, in the search for alternative agents having an antimicrobial and in particular preserving action it is to be noted that the substances used in the cosmetics, pharmaceutical and/or foodstuffs field must be

- toxicologically acceptable
- readily tolerated by the skin
- stable (in particular in the conventional cosmetic and/or pharmaceutical formulations)
- inexpensive to prepare (i.e. employing standard processes and/or starting from standard precursors)
- easy to formulate (i.e. preferably liquid) and should not be detrimental to the final product.
- of favorable taste and odor in order to allow blending them into different flavour and fragrances without altering significantly their sensory characteristics.

Furthermore, they should have antimicrobial activity characteristics, which fulfill the diverse criteria. They should

- provide a broad-spectrum anti-microbial activity against gram positive and gram negative bacteria, yeast and mold
- show a particularly strong activity against the mold *A. brasiliensis*
- be active in different cosmetic formulations at different pH values.

From the state of the art numerous publications are known dealing with various types of products that are active against micro-organisms. However, few have identified compounds or mixtures of compounds that provide broad spectrum preservative efficacy of cosmetic products.

For example, Natsch evaluated combinations of aromatic alcohols and benzaldehydes, which can enable preservation of cosmetic formulations against different bacteria, yeast and mould. The here described lactate esters, however, are not part of this invention (WO 2007 071089 A1, GIVAUDAN).

US 2006/110415 A1 (BIODERM RESEARCH) discloses the use of topical compositions including esters of hydroxy acids in the deep penetration delivery of beneficial cosmetic and pharmaceutical agents. Different lactate esters, e.g. butyl, pentyl or benzyl lactate is described for this purpose. No combinations with other flavor or fragrance molecules as described here are mentioned.

Kawasaki describes yogurt-like flavour composition containing benzyl lactate (JP 2006124490). These flavours do not comprise combinations of benzyl lactate with aromatic alcohols, aldehyds, or acids such as claimed here.

Granett claims preparations capable of repelling various insects. Benzyl lactate is among the substances contained in the preparations. No combinations with flavor or fragrance molecules as described here are mentioned (U.S. Pat. No. 2,274,267 A, NATIONAL CARBON).

US 2006 067990A1 (Kimberly-Clark Worldwide, Inc.) discloses use of absorbent articles to inhibit exo-protein production of gram positive bacteria, shown with the example of *S. aureus*. Benzyl lactate is one of the compounds found to be active in this invention. No combinations with flavor or fragrance molecules as described here are mentioned.

US 2006 067991A1 (Kimberly-Clark Worldwide, Inc.) discloses use of non-absorbent articles to inhibit exo-protein production of gram positive bacteria, shown with the example of *S. aureus*. Benzyl lactate is one of the compounds found to be active in this invention. No combinations with flavor or fragrance molecules as described here are mentioned.

The search for suitable (active) substances, which have one or more of the properties mentioned to an adequate extent is made difficult for the person skilled in the art in that there is no clear dependency between the chemical structure of a substance on the one hand and its biological activity against certain microorganisms (bacteria, yeast, fungi, small eukaryotes) on the other hand. This makes testing of substances in laboratory experiments inevitable. In addition, the antimicrobial performance in cosmetic formulation cannot be derived from standard anti-microbial screening tests, such as growth inhibition experiments as described in e.g. DIN 58940 or ISO 20776. Many antimicrobial substances characterized by low minimum inhibitory concentrations (MICS) fail to perform in more advanced and applied assays. For product preservation, the highly laborious and time-consuming "challenge test" according to ISO 11930, European Pharmacopoeia 7-5.1.3, or United States Pharmacopoeia 35 has to be used. Furthermore, there is no predictable connection between the chemical structure and other physico-chemical parameters relevant to the field of cosmetics, i.e. the toxicological acceptability, the skin tolerability, the stability, solubility and formulation properties and the smell and taste of a substance.

Therefore, the problem underlying the present invention has been developing new antimicrobial agents and combinations that fulfill the complex profile explained above and are particularly active at low concentrations against a variety of different micro-organisms.

DESCRIPTION OF THE INVENTION

Object of the present invention is a composition, preferably an antimicrobial composition, comprising
(a) at least one lactate ester of formula (I)

in which R stands for hydrogen or linear or branched $C_1$-$C_{10}$-alkyl, which is optionally substituted with hydroxy or methoxy or $C_1$-$C_4$-alkyl or linear or branched $C_1$-$C_{10}$-alkoxy, which is optionally substituted with hydroxy or methoxy or $C_1$-$C_4$-alkyl or linear or branched $C_1$-$C_{10}$ alkenyl, which is optionally substituted with hydroxy or methoxy or $C_1$-$C_4$-alkyl or $C_3$-$C_{10}$-cycloalkyl, which is optionally substituted with hydroxy or methoxy or $C_1$-$C_4$-alkyl or $C_3$-$C_{10}$-cycloalkenyl, which is optionally substituted with hydroxy or methoxy or $C_1$-$C_4$-alkyl or benzyl or a cosmetically or pharmaceutically acceptable salt thereof, and (b1) at least one benzaldehyde derivative of formula (II)

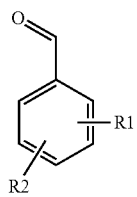

(II)

in which R1 and R2 independently stand for hydrogen, methyl, hydroxy, or methoxy or a cosmetically or pharmaceutically acceptable salt thereof, and/or (b2) at least one aromatic alcohol of formula (IIIa) and/or (IIIb)

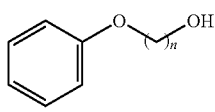

(IIIa)

in which n stands for 1, 2 or 3, or a cosmetically or pharmaceutically acceptable salt thereof,

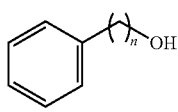

(IIIb)

in which n stands for 1, 2 or 3 or a cosmetically or pharmaceutically acceptable salt thereof, and/or (b3) at least one aromatic acid of formula (IV).

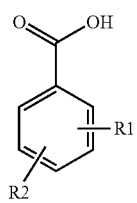

(IV)

in which R1 and R2 independently stand for H, methyl, hydroxy, or methoxy or a cosmetically or pharmaceutically acceptable salt thereof.

Preferably the compositions according to the present invention encompass at least one species selected from group (a) and at least one two other species, each of them selected from group (b1 and b2) or (b2 and b3) or (b1 and b3).

Preferably the compositions are free of biocides as listed in Annex V of the Cosmetic Directive, more preferably they do not contain any parabens or formaldehyde donators.

Surprisingly, it has been observed that compositions of compounds of formula (I) in combination with compounds of formula (II), (III), and/or (IV) according to the invention show a very good broad spectrum activity as agents to preserve various formulations against microbial spoilage. Furthermore, these compositions synergistically intensified antimicrobial effects at least against selected microorganisms, in particular against mould species of the genus *Aspergillus*, such as *Aspergillus brasiliensis, niger, flavus, fumigatus* and also other microorganisms, such as *Candida albicans, Escherichia coli*, and *Staphylococcus aureus*. Moulds are known to be combated only with great difficulty, due to their high tolerance for different pH, temperature, osmotic pressure and nutrient conditions as well as their ability to resist to and degrade different chemicals.

In particular, it has been found that the mixtures according to the invention can be used outstandingly as an antimicrobial active compound mixture, in particular for preserving otherwise perishable articles.

More particularly it was found that the synergistically active mixtures according to the invention have a good action against *Staphylococcus epidermidis, Corynebacterium xerosis, Brevibacterium epidermidis, Propionibacterium acnes* and against *Trichophyton* and *Epidermophyton* species, so that they can be employed as agents for the treatment or the combating of underarm and foot odour or body odour generally, as agents for combating acne, as anti-dandruff agents and for the treatment of mycoses, in particular dermatocyceses.

Lactate Esters

Lactate esters according to the present invention (group a) represent known compounds that can be obtained by ordinary methods of organic chemistry. It is understood that R can be of different chain length and of aliphatic and aromatic character.

Preferably, the species are selected from the group consisting of

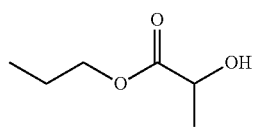

(Ia)

propyl lactate

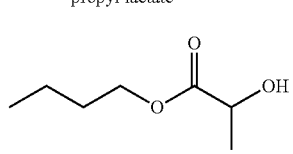

(Ib)

butyl lactate

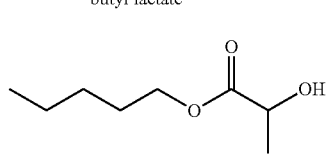

(Ic)

pentyl lactate

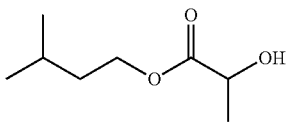

isopentyl lactate (Id)

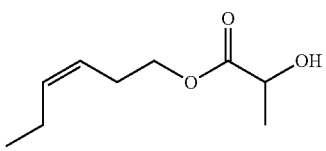

cis hexenyl lactate (Ie)

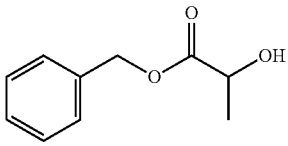

benzyl lactate (If)

or their mixtures. In as far the definition refers to cosmetically or pharmaceutically acceptable salts of said lactate esters, this means that these salts can be safely used for pharmaceutical purposes. This does not mean that the present invention or any aspect thereof is restricted to the use of a compound of formula (I) or a corresponding mixture for pharmaceutical purposes. Generally, if a salt can be used for pharmaceutical purposes it can likewise be used for cosmetic purposes, or in food or beverage formulations. In particular, the sodium and potassium and ammonium salts of compounds of formula (I) are considered as (pharmaceutically) acceptable salts. In some cases the utilization of the respective ionic compound or solvate carrier proves to be superior to the unmodified lactate esters. The (pharmaceutically) acceptable salts (and the corresponding solvates) of compounds of formula (I) can be prepared by standard procedures. Hereinafter, any reference to a compound of formula (I) or a corresponding mixture as defined above is to be understood as comprising an additional reference to corresponding (pharmaceutically) acceptable salts thereof.

It is also worth to be mentioned that although persons skilled in the art have already addressed the antimicrobial properties of aromatic aldehydes, e.g. benzaldehyde, 4-hydroxy benzaldehyde, 4-methoxy benzaldehyde, aromatic alcohols, e.g. benzyl alcohol, 2-phenylethyl alcohol, 3-phenylpropanol, 2-phenoxyethanol, and aromatic acids, e.g. benzoic acid, 4-hydroxy benzoic acid, 4-methoxy benzoic acid extensively, there has hitherto been no indication that mixtures of the lactate esters have a significantly improved antimicrobial action (at least against selected microorganisms) in the individual case. It was therefore particularly surprising that the mixtures according to the invention show a highly synergistic activity, and in the treatment of moulds of the genus *Aspergillus* are significantly superior to individually dosed compounds of the formula (I) or individually dosed compounds of the formula (II), (III), or (IV) at the same concentration, in particular in respect of the reduction in microbial counts and the speed of the reduction in microbial count.

In a preferred mixture, compounds of formula (I) are used at 0.05 to 1% b.w. and combined with compounds of formula (II), (III), or (IV) at 0.05 to 0.5% b.w.

Benzaldehyde Derivatives

Benzaldehyde derivatives, forming group (b1) are represented by formula (II)

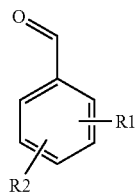

(II)

in which R1 and R2 independently stand for H, methyl, hydroxy, or methoxy or R1 and R2 forms a 3,4-methylendioxy substituent, or a cosmetically or pharmaceutically acceptable salt thereof. Preferred examples encompass species for formula (II) wherein if R1 is hydrogen then R2 is selected from methyl, hydroxy and methoxy, or wherein if R1 is hydroxy, then R2 is selected from hydrogen, hydroxy and methoxy.

Preferred examples also encompass 4-methylbenzaldehyde, heliotropine, vanillin, 4-hydroxybenzaldehyde, 3-hydroxybenzaldehyde, 4-methoxybenzaldehyde, 3-methoxybenzaldehyde, 2-hydroxibenzaldehyde, 3-hydroxy-4-methoxybenzaldehyde, 3,5-dihydroxybenzaldehyde, 4-hydroxy-2-methoxybenzaldehyde or their mixtures.

Aromatic Alcohols

Suitable aromatic alcohols (group b2) following formula (IIIa) or (IIIb)

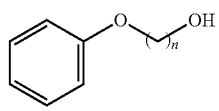

(IIIa)

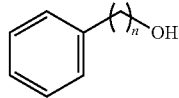

(IIIb)

in which n stands for 1, 2 or 3 encompass for example phenoxymethanol, phenoxypropanol and in particular phenoxyethanol.

Aromatic Acids

Suitable aromatic acids (group b3) following formula (IV)

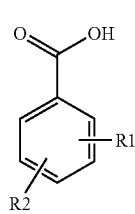

(IV)

in which R1 and R2 independently stand for hydrogen, methyl, hydroxy, or methoxy encompass 2-methylbenzoic acid, 3-methylbenzoic acid, 4-methylbenzoic acid, 2-hydroxy benzoic acid, 3-hydroxybenzoic acid, 4-hydroxybenzoic acid, 2-methoxybenzoic acid, 3-methoxybenzoic acid, 4-methoxybenzoic acid and for example their sodium, potassium, ammonium, alkylammonium and glucammonium salts.

The antimicrobial compositions may contain compound (a) and the sum of compounds (b1+b2+b3) in a ratio by weight that ranges from 99:1 to 1:99, preferably from about 90:10 to about 10:90, more preferably from about 75:25 to about 25:75 and most preferably from about 60:40 to about 40:60.

Preferably, each of the components of the composition according to the present invention are present in amounts of at least 500 ppm, and more preferably of at least 750 ppm, and most preferably of at least 900 ppm.

Cosmetic or Personal Care Compositions

Another object of the present invention encompasses a cosmetic or personal care composition comprising said antimicrobial compositions. The cosmetic or personal care composition may represent for example a skin care, hair care and/or sun care product or a fragrance composition, such as for example a cosmetic cream, lotion, spray, emulsion, ointment, gel or mouse and the like. Typical examples are skin creams and hair shampoos, antiperspirants and soaps.

The antimicrobial composition may be added to said cosmetic or personal care composition in an amount of about 0.05 to about 2% b.w., preferably in an amount of about 0.1 to about 1.5% b.w. and more preferably in an amount of about 0.75 to about 1% b.w.—calculated on the total composition.

The preparations according to the invention may contain abrasives, anti-acne agents, agents against ageing of the skin, anti-cellulitis agents, antidandruff agents, anti-inflammatory agents, irritation-preventing agents, irritation-inhibiting agents, antioxidants, astringents, perspiration-inhibiting agents, antiseptic agents, ant-statics, binders, buffers, carrier materials, chelating agents, cell stimulants, cleansing agents, care agents, depilatory agents, surface-active substances, deodorizing agents, antiperspirants, softeners, emulsifiers, enzymes, essential oils, fibres, film-forming agents, fixatives, foam-forming agents, foam stabilizers, substances for preventing foaming, foam boosters, gelling agents, gel-forming agents, hair care agents, hair-setting agents, hair-straightening agents, moisture-donating agents, moisturizing substances, moisture-retaining substances, bleaching agents, strengthening agents, stain-removing agents, optically brightening agents, impregnating agents, dirtrepellent agents, friction-reducing agents, lubricants, moisturizing creams, ointments, opacifying agents, plasticizing agents, covering agents, polish, gloss agents, polymers, powders, proteins, re-oiling agents, abrading agents, silicones, skin-soothing agents, skin-cleansing agents, skin care agents, skin-healing agents, skin-lightening agents, skin-protecting agents, skin-softening agents, hair promotion agents, cooling agents, skin-cooling agents, warming agents, skin-warming agents, stabilizers, UV-absorbing agents, UV filters, detergents, fabric conditioning agents, suspending agents, skin-tanning agents, thickeners, vitamins, oils, waxes, fats, phospholipids, saturated fatty acids, mono- or polyunsaturated fatty acids, α-hydroxy acids, polyhydroxy fatty acids, liquefiers, dyestuffs, colour-protecting agents, pigments, anti-corrosives, aromas, flavouring substances, odoriferous substances, polyols, surfactants, electrolytes, organic solvents or silicone derivatives and the like as additional auxiliaries and additives.

Surfactans

Preferred auxiliaries and additives are anionic and/or amphoteric or zwitterionic surfactants. Typical examples of anionic surfactants are soaps, alkyl benzenesulfonates, alkanesulfonates, olefin sulfonates, alkylether sulfonates, glycerol ether sulfonates, methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside and Mineralöladditive (Catalysts, Surfactants and Mineral Oil Additives)", Thieme Verlag, Stuttgart, 1978, pages 123-217. The percentage content of surfactants in the preparations may be from 0.1 to 10% by weight and is preferably from 0.5 to 5% by weight, based on the preparation.

Oil Bodies

Suitable oil bodies, which form constituents of the O/W emulsions, are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

Emulsifiers

Other surfactants may also be added to the preparations as emulsifiers, including for example:

- products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;
- $C_{12/18}$ fatty acid monoesters and diesters of addition products of 1 to 30 mol ethylene oxide onto glycerol;
- glycerol mono- and diesters and sorbitan mono- and diesters of saturated and unsaturated fatty acids containing 6 to 22 carbon atoms and ethylene oxide addition products thereof;
- addition products of 15 to 60 mol ethylene oxide onto castor oil and/or hydrogenated castor oil;
- polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;
- addition products of 2 to 15 mol ethylene oxide onto castor oil and/or hydrogenated castor oil;
- partial esters based on linear, branched, unsaturated or saturated $C_{6/22}$ fatty acids, ricinoleic acid and 12-hydroxystearic acid and glycerol, polyglycerol, pentaerythritol, -dipentaerythritol, sugar alcohols (for example sorbitol), alkyl glucosides (for example methyl glucoside, butyl glucoside, lauryl glucoside) and polyglucosides (for example cellulose);
- mono-, di and trialkyl phosphates and mono-, di- and/or tri-PEG-alkyl phosphates and salts thereof;
- wool wax alcohols;
- polysiloxane/polyalkyl polyether copolymers and corresponding derivatives;
- mixed esters of pentaerythritol, fatty acids, citric acid and fatty alcohol and/or mixed esters of $C_{6-22}$ fatty acids, methyl glucose and polyols, preferably glycerol or polyglycerol,
- polyalkylene glycols and
- glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

Partial Glycerides.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Sorbitan Esters.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol Esters.

Typical examples of suitable polyglycerol esters are Polyglyceryl-2 Dipolyhydroxystearate (Dehymuls®PGPH), Polyglycerin-3-Diisostearate (Lameform®TGI), Polyglyceryl-4 Isostearate (Isolan®GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Anionic Emulsifiers.

Typical anionic emulsifiers are aliphatic $C_{12-22}$ fatty acids, such as palmitic acid, stearic acid or behenic acid for example, and $C_{12-22}$ dicarboxylic acids, such as azelaic acid or sebacic acid for example.

Amphoteric Emulsifiers.

Other suitable emulsifiers are amphboteric or zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8\text{-}18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12\text{-}18}$ acyl sarcosine.

Superfatting Agents and Consistency Factors

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Thickening Agents and Rheology Additives

Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

Polymers

Suitable cationic polymers are, for example, cationic cellulose derivatives such as, for example, the quaternized hydroxyethyl cellulose obtainable from Amerchol under the name of PolynnerJR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bisdimethylamino-1,3-propane, cationic guar gum such as, for example, Jaguar® CBS, Jaguar®C-17, Jaguar®C-16 of Celanese, quaternized ammonium salt polymers such as, for example, Mirapor®A-15, Mirapol®AD-1, Mirapol®AZ-1 of Miranol and the various polyquaternium types (for example 6, 7, 32 or 37) which can be found in the market under the tradenames Rheocare® CC or Ultragel® 300.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Pearlizing Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Silicones

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Waxes and Stabilizers

Besides natural oils used, waxes may also be present in the preparations, more especially natural waxes such as, for example, candelilla wax, carnauba wax, Japan wax, espartograss wax, cork wax, *guaruma* wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

Primary Sun Protection Factors

Primary sun protection factors in the context of the invention are, for example, organic substances (light filters) which are liquid or crystalline at room temperature and which are capable of absorbing ultraviolet radiation and of releasing the energy absorbed in the form of longer-wave radiation, for example heat.

The formulations according to the invention advantageously contain at least one UV-A filter and/or at least one UV-B filter and/or a broadband filter and/or at least one inorganic pigment. Formulations according to the invention preferably contain at least one UV-B filter or a broadband filter, more particularly preferably at least one UV-A filter and at least one UV-B filter.

Preferred cosmetic compositions, preferably topical formulations according to the present invention comprise one, two, three or more sun protection factors selected from the group consisting of 4-aminobenzoic acid and derivatives, salicylic acid derivatives, benzophenone derivatives, dibenzoylmethane derivatives, diphenyl acrylates, 3-imidazol-4-yl acrylic acid and esters thereof, benzofuran derivatives, benzylidene malonate derivatives, polymeric UV absorbers containing one or more organosilicon radicals, cinnamic acid derivatives, camphor derivatives, trianilino-s-triazine derivatives, 2-hydroxyphenylbenzotriazole derivatives, phenylbenzimidazole sulfonic acid derivatives and salts thereof, anthranilic acid menthyl esters, benzotriazole derivatives and indole derivatives.

In addition, it is advantageous to combine compounds of formula (I) with active ingredients which penetrate into the skin and protect the skin cells from inside against sunlight-induced damage and reduce the level of cutaneous matrix metalloproteases. Preferred respective ingredients, so called arylhydrocarbon receptor antagonists, are described in WO 2007/128723, incorporated herein by reference. Preferred is 2-benzylidene-5,6-dimethoxy-3,3-dimethylindan-1-one.

The UV filters cited below which can be used within the context of the present invention are preferred but naturally are not limiting.

UV filters which are preferably used are selected from the group consisting of
p-aminobenzoic acid
p-aminobenzoic acid ethyl ester (25 mol) ethoxylated (INCI name: PEG-25 PABA)
p-dimethylaminobenzoic acid-2-ethylhexyl ester
p-aminobenzoic acid ethyl ester (2 mol) N-propoxylated
p-aminobenzoic acid glycerol ester
salicylic acid homomenthyl ester (homosalates) (Neo Heliopan®MS)
salicylic acid-2-ethylhexyl ester (Neo Heliopan®OS)
triethanolamine salicylate
4-isopropyl benzyl salicylate
anthranilic acid menthyl ester (Neo Heliopan®MA)
diisopropyl cinnamic acid ethyl ester
p-methoxycinnamic acid-2-ethylhexyl ester (Neo Heliopan®AV)
diisopropyl cinnamic acid methyl ester
p-methoxycinnamic acid isoamyl ester (Neo Heliopan®E 1000)
p-methoxycinnamic acid diethanolamine salt
p-methoxycinnamic acid isopropyl ester
2-phenylbenzimidazole sulfonic acid and salts (Neo Heliopan®Hydro)
3-(4'-trimethylammonium)benzylidene bornan-2-one methyl sulfate
beta-imidazole-4(5)-acrylic acid (urocanic acid)
3-(4'-sulfo)benzylidene bornan-2-one and salts
3-(4'-methyl benzylidene)-D,L-camphor (Neo Heliopan®MBC)
3-benzylidene-D,L-camphor
N-[(2 and 4)-[2-(oxoborn-3-ylidene)methyl]benzyl]acrylamide polymer
4,4'-[(6-[4-(1,1-dimethyl)aminocarbonyl)phenylamino]-1,3,5-triazine-2,4-diyl)diimino]-bis-(benzoic acid-2-ethylhexyl ester) (Uvasorb®HEB)
benzylidene malonate polysiloxane (Parsol®SLX)
glyceryl ethylhexanoate dimethoxycinnamate
dipropylene glycol salicylate
tris(2-ethylhexyl)-4,4',4"-(1,3,5-triazine-2,4,6-triyltriimino) tribenzoate (=2,4,6-trianilino-(p-carbo-2'-ethylhexyl-r-oxy)-1,3,5-triazine) (Uvinul®T150).

Broadband filters which are preferably combined with one or more compounds of formula (I) in a preparation according to the present invention are selected from the group consisting of
2-ethylhexyl-2-cyano-3,3-diphenyl acrylate (Neo Heliopan®303)
ethyl-2-cyano-3,3'-diphenyl acrylate
2-hydroxy-4-methoxybenzophenone (Neo Heliopan®BB)
2-hydroxy-4-methoxybenzophenone-5-sulfonic acid
dihydroxy-4-methoxybenzophenone
2,4-dihydroxybenzophenone
tetrahydroxybenzophenone
2,2'-dihydroxy-4,4'-dimethoxybenzophenone
2-hydroxy-4-n-octoxybenzophenone
2-hydroxy-4-methoxy-4'-methyl benzophenone
sodium hydroxymethoxybenzophenone sulfonate
disodium-2,2'-dihydroxy-4,4'-dimethoxy-5,5'-disulfobenzophenone
phenol, 2-(2H-benzotriazol-2-yl)-4-methyl-6-(2-methyl-3 (1,3,3,3-tetramethyl-1-(trimethylsilyl)oxy)disiloxanyl) propyl) (Mexoryl®XL)
2,2'-methylene bis-(6-(2H-benzotriazol-2-yl)-4-1,1,3,3-tetramethylbutyl)phenol) (Tinosorb®M)
2,4-bis-[4-(2-ethylhexyloxy)-2-hydroxyphenyl]-1,3,5-triazine
2,4-bis-[{(4-(2-ethylhexyloxy)-2-hydroxy}phenyl]-6-(4-methoxyphenyl)-1,3,5-triazine (Tinosorb®S)
2,4-bis-[{(4-(3-sulfonato)-2-hydroxypropyloxy)-2-hydroxy}phenyl]-6-(4-methoxyphenyl)-1,3,5-triazine sodium salt
2,4-bis-[{(3-(2-propyloxy)-2-hydroxypropyloxy)-2-hydroxy}phenyl]-6-(4-methoxyphenyl)-1,3,5-triazine
2,4-bis-[{4-(2-ethylhexyloxy)-2-hydroxy}phenyl]-6-[4-(2-methoxyethyl carbonyl)phenylamino]-1,3,5-triazine
2,4-bis-[{4-(3-(2-propyloxy)-2-hydroxypropyloxy)-2-hydroxy}phenyl]-6-[4-(2-ethylcarboxyl)phenylamino]-1,3,5-triazine
2,4-bis-[{4-(2-ethylhexyloxy)-2-hydroxy}phenyl]-6-(1-methylpyrrol-2-yl)-1,3,5-triazine
2,4-bis-[{4-tris-(trimethylsiloxysilylpropyloxy)-2-hydroxy}phenyl]-6-(4-methoxyphenyl)-1,3,5-triazine
2,4-bis-[{4-(2"-methylpropenyloxy)-2-hydroxy}phenyl]-6-(4-methoxyphenyl)-1,3,5-triazine
2,4-bis-[{4-(1',1',1',3',5',5',5'-heptamethylsiloxy-2"-methyl propyloxy)-2-hydroxy}phenyl]-6-(4-methoxyphenyl)-1,3,5-triazine.

The compositions can comprise further typical detergent and cleansing composition ingredients such as UV-A filters filters which are preferably combined with one or more compounds of formula (I) in a preparation according to the present invention are selected from the group consisting of
4-isopropyl dibenzoyl methane
terephthalylidene dibornane sulfonic acid and salts (Mexoryl®SX)
4-t-butyl-4'-methoxydibenzoyl methane (avobenzone)/(Neo Heliopan®357)
phenylene bis-benzimidazyl tetrasulfonic acid disodium salt (Neo Heliopan®AP)

2,2'-(1,4-phenylene)-bis-(1H-benzimidazole-4,6-disulfonic acid), monosodium salt
2-(4-diethylamino-2-hydroxybenzoyl)benzoic acid hexyl ester (Uvinul® A Plus)
indanylidene compounds in accordance with DE 100 55 940 A1 (=WO 2002 038537 A1)

The compositions can comprise further typical detergent and cleansing composition ingredients such as UV filters which are more preferably combined with one or more compounds of formula (I) in a preparation according to the present invention are selected from the group consisting of p-aminobenzoic acid
3-(4'-trimethylammonium)benzylidene bornan-2-one methyl sulfate
salicylic acid homomenthyl ester (Neo Heliopan®HMS)
2-hydroxy-4-methoxybenzophenone (Neo Heliopan®BB)
2-phenylbenzimidazole sulfonic acid (Neo Heliopan®Hydro)
terephthalylidene dibornane sulfonic acid and salts (Mexoryl®SX)
4-tert-butyl-4'-methoxydibenzoyl methane (Neo Heliopan®357)
3-(4'-sulfo)benzylidene bornan-2-one and salts
2-ethylhexyl-2-cyano-3,3-diphenyl acrylate (Neo Heliopan®303)
N-[(2 and 4)-[2-(oxoborn-3-ylidene)methyl]benzyl]acrylamide polymer
p-methoxycinnamic acid-2-ethylhexyl ester (Neo Heliopan®AV)
p-aminobenzoic acid ethyl ester (25 mol) ethoxylated (INCI name: PEG-25 PABA)
p-methoxycinnamic acid isoamyl ester (Neo Heliopan®E1000)
2,4,6-trianilino-(p-carbo-2'-ethylhexyl-1'-oxy)-1,3,5-triazine (Uvinul®T150)
phenol, 2-(2H-benzotriazol-2-yl)-4-methyl-6-(2-methyl-3 (1,3,3,3-tetramethyl-1-(trimethylsilyl)oxy)disiloxyanyl) propyl) (Mexoryl®XL)
4,4'-[(6-[4-(1,1-dimethyl)aminocarbonyl)phenylamino]-1,3, 5-triazine-2,4-diyl)diimino]-bis-(benzoic acid-2-ethylhexyl ester) (Uvasorb HEB)
3-(4'-methyl benzylidene)-D,L-camphor (Neo Heliopan®MBC)
3-benzylidene camphor
salicylic acid-2-ethylhexyl ester (Neo Heliopan®OS)
4-dimethylaminobenzoic acid-2-ethylhexyl ester (Padimate O)
hydroxy-4-methoxybenzophenone-5-sulfonic acid and Na salt
2,2'-methylene bis-(6-(2H-benzotriazol-2-yl)-4-1,1,3,3-tetramethylbutyl)phenol) (Tinosorb®M)
phenylene bis-benzimidazyl tetrasulfonic acid disodium salt (Neo Heliopan®AP)
2,4-bis-[{(4-(2-ethylhexyloxy)-2-hydroxy}phenyl]-6-(4-methoxyphenyl)-1,3,5-triazine (Tinosorb®S)
benzylidene malonate polysiloxane (Parsol®SLX)
menthyl anthranilate (Neo Heliopan®MA)
2-(4-diethylamino-2-hydroxybenzoyl)benzoic acid hexyl ester (Uvinul® A Plus)
indanylidene compounds in accordance with DE 100 55 940 (=WO 02/38537).

Advantageous primary and also secondary sun protection factors are mentioned in WO 2005 123101 A1. Advantageously, these preparations contain at least one UVA filter and/or at least one UVB filter and/or at least one inorganic pigment. The preparations may be present here in various forms such as are conventionally used for sun protection preparations. Thus, they may be in form of a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

In a further preferred embodiment a formulation according to the invention contains a total amount of sunscreen agents, i.e. in particular UV filters and/or inorganic pigments (UV filtering pigments) so that the formulation according to the invention has a light protection factor of greater than or equal to 2 (preferably greater than or equal to 5). Such formulations according to the invention are particularly suitable for protecting the skin and hair.

Secondary Sun Protection Factors

Besides the groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example alpha-carotene, beta-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, alpha-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages, also (metal) chelators (for example alpha-hydroxyfatty acids, palmitic acid, phytic acid, lactoferrine), alpha-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, titanium dioxide (for example dispersions in ethanol), zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Advantageous inorganic secondary light protection pigments are finely dispersed metal oxides and metal salts which are also mentioned in WO 2005 123101 A1. The total quantity of inorganic pigments, in particular hydrophobic inorganic micro-pigments in the finished cosmetic preparation according to the present invention is advantageously from 0.1 to 30% by weight, preferably 0.5 to 10.0% by weight, in each case based on the total weight of the preparation.

Also preferred are particulate UV filters or inorganic pigments, which can optionally be hydrophobed, can be used, such as the oxides of titanium ($TiO_2$), zinc (ZnO), iron ($Fe_2O_3$), zirconium ($ZrO_2$), silicon ($SiO_2$), manganese (e.g. MnO), aluminium ($Al_2O_3$), cerium (e.g. $Ce_2O_3$) and/or mixtures thereof.

Actives Modulating Skin and/or Hair Pigmentation

Preferred active ingredients for skin and/or hair lightening are selected from the group consisting of: kojic acid (5-hydroxy-2-hydroxymethyl-4-pyranone), kojic acid derivatives, preferably kojic acid dipalmitate, arbutin, ascorbic acid, ascorbic acid derivatives, preferably magnesium ascorbyl phosphate, hydroquinone, hydroquinone derivatives, resorcinol, resorcinol derivatives, preferably 4-alkylresorcinols and 4-(1-phenylethyl)1,3-dihydroxybenzene (phenylethyl resorcinol), cyclohexylcarbamates (preferably one or more cyclohexyl carbamates disclosed in WO 2010/122178 and WO 2010/097480), sulfurcontaining molecules, preferably glutathione or cysteine, alpha-hydroxy acids (preferably citric acid, lactic acid, malic acid), salts and esters thereof, N-acetyl tyrosine and derivatives, undecenoyl phenylalanine, gluconic acid, chromone derivatives, preferably aloesin, flavonoids, 1-aminoethyl phosphinic acid, thiourea derivatives, ellagic acid, nicotinamide (niacinamide), zinc salts, preferably zinc chloride or zinc gluconate, thujaplicin and derivatives, triterpenes, preferably maslinic acid, sterols, preferably ergosterol, benzofuranones, preferably senkyunolide, vinyl guiacol, ethyl guiacol, dionic acids, preferably octodecene dionic acid and/or azelaic acid, inhibitors of nitrogen oxide synthesis, preferably L-nitroarginine and derivatives thereof, 2,7-dinitroindazole or thiocitrulline, metal chelators (preferably alpha-hydroxy fatty acids, phytic acid, humic acid, bile acid, bile extracts, EDTA, EGTA and derivatives thereof), retinoids, soy milk and extract, serine protease inhibitors or lipoic acid or other synthetic or natural active ingredients for skin and hair lightening, the latter preferably used in the form of an extract from plants, preferably bearberry extract, rice extract, *papaya* extract, turmeric extract, mulberry extract, bengkoang extract, nutgrass extract, liquorice root extract or constituents concentrated or isolated therefrom, preferably glabridin or licochalcone A, *artocarpus* extract, extract of *rumex* and *ramulus* species, extracts of pine species (*pinus*), extracts of *vitis* species or stilbene derivatives isolated or concentrated therefrom, saxifrage extract, scutelleria extract, grape extract and/or microalgae extract, in particular *Tetraselmis suecica* Extract.

Preferred skin lighteners as component (b) are kojic acid and phenylethyl resorcinol as tyrosinase inhibitors, beta- and alpha-arbutin, hydroquinone, nicotinamide, dioic acid, Mg ascorbyl phosphate and vitamin C and its derivatives, mulberry extract, Bengkoang extract, *papaya* extract, turmeric extract, nutgrass extract, licorice extract (containing glycyrrhizin), alpha-hydroxy-acids, 4-alkylresorcinols, 4-hydroxyanisole. These skin lighteners are preferred due to their very good activity, in particular in combination with sclareolide according to the present invention. In addition, said preferred skin lighteners are readily available.

Advantageous skin and hair tanning active ingredients in this respect are substrates or substrate analogues of tyrosinase such as L-tyrosine, N-acetyl tyrosine, L-DOPA or L-dihydroxyphenylalanine, xanthine alkaloids such as caffeine, theobromine and theophyl-line and derivatives thereof, proopiomelanocortin peptides such as ACTH, alpha-MSH, peptide analogues thereof and other substances which bind to the melanocortin receptor, peptides such as Val-Gly-Val-Ala-Pro-Gly, Lys-Ile-Gly-Arg-Lys or Leu-Ile-Gly-Lys, purines, pyrimidines, folic acid, copper salts such as copper gluconate, chloride or pyrrolidonate, 1,3,4-oxadiazole-2-thiols such as 5-pyrazin-2-yl-1,3,4-oxadiazole-2-thiol, curcumin, zinc diglycinate (Zn(Gly)2), manganese(II) bicarbonate complexes ("pseudocat-alases") as described for example in EP 0 584 178, tetrasubstituted cyclohexene deriva-tives as described for example in WO 2005/032501, isoprenoids as described in WO 2005/102252 and in WO 2006/010661, melanin derivatives such as Melasyn-100 and MelanZe, diacyl glycerols, aliphatic or cyclic diols, psoralens, prostaglandins and ana-logues thereof, activators of adenylate cyclase and compounds which activate the transfer of melanosomes to keratinocytes such as serine proteases or agonists of the PAR-2 receptor, extracts of plants and plant parts of the *chrysanthemum* species, san-guisorba species, walnut extracts, urucum extracts, rhubarb extracts, microalgae extracts, in particular *Isochrysis galbana*, trehalose, erythru-lose and dihydroxyacetone. Flavonoids which bring about skin and hair tinting or brown-ing (e.g. quercetin, rhamnetin, kaempferol, fisetin, genistein, daidzein, chrysin and api-genin, epicatechin, diosmin and diosmetin, morin, quercitrin, naringenin, hesperidin, phloridzin and phloretin) can also be used.

The amount of the aforementioned examples of additional active ingredients for the modulation of skin and hair pigmentation (one or more compounds) in the products according to the invention is then preferably 0.00001 to 30 wt. %, preferably 0.0001 to 20 wt. %, particularly preferably 0.001 to 5 wt. %, based on the total weight of the preparation.

Anti-Ageing Actives

In the context of the invention, anti-ageing or biogenic agents are, for example antioxidants, matrix-metalloproteinase inhibitors (MMPI), skin moisturizing agents, glycosaminglycan stimulators, anti-inflammatory agents, TRPV1 antagonists and plant extracts.

Antioxidants.

Suitable antioxidants encompass amino acids (preferably glycine, histidine, tyrosine, tryptophane) and derivatives thereof, imidazoles (preferably urocanic acid) and derivatives thereof, peptides, preferably D,L-carnosine, D-carnosine, L-carnosine and derivatives thereof (preferably anserine), carnitine, creatine, matrikine peptides (preferably lysyl-threonyl-threonyl-lysyl-serine) and palmitoylated pentapeptides, carotenoids, carotenes (preferably alpha-carotene, beta-carotene, lycopene) and derivatives thereof, lipoic acid and derivatives thereof (preferably dihydrolipoic acid), aurothioglucose, propyl thiouracil and other thiols (preferably thioredoxine, glutathione, cysteine, cystine, cystamine and glycosyl, N-acetyl, methyl, ethyl, propyl, amyl, butyl and lauryl, palmitoyl, oleyl, gamma-linoleyl, cholesteryl, glyceryl and oligoglyceryl esters thereof) and salts thereof, dilauryl thiodipropionate, distearyl thiodipropionate, thiodipropionic acid and derivatives thereof (preferably esters, ethers, peptides, lipids, nucleotides, nucleosides and salts) and sulfoximine compounds (preferably buthionine sulfoximines, homocysteine sulfoximine, buthionine sulfones, penta-, hexa-, heptathionine sulfoximine) in very small tolerated doses (e.g. pmol to µmol/kg), also (metal) chelators (preferably alpha-hydroxy fatty acids, palmitic acid, phytic acid, lactoferrin, alpha-hydroxy acids (preferably citric acid, lactic acid, malic acid), humic acid, bile acid, bile extracts, tannins, bilirubin, biliverdin, EDTA, EGTA and derivatives thereof), unsaturated fatty acids and derivatives thereof (preferably gamma-linolenic acid, linoleic acid, oleic acid), folic acid and derivatives thereof, ubiquinone and derivatives thereof, ubiquinol and derivatives thereof, vitamin C and derivatives (preferably ascorbyl palmitate, Mg ascorbyl phosphate, ascorbyl acetate, ascorbyl glucoside), tocopherols and derivatives (preferably vitamin E acetate), vitamin A and derivatives (vitamin A palmitate) and coniferyl benzoate of benzoic resin, rutinic acid and derivatives thereof, flavonoids and glycosylated precursors thereof, in particular quercetin and derivatives thereof, preferably alpha-glucosyl rutin, rosmarinic acid, carnosol, carnosolic acid, resveratrol, caffeic acid and derivatives thereof, sinapic acid and derivatives thereof, ferulic acid and derivatives thereof, curcuminoids, chlorogenic acid and derivatives thereof, retinoids, preferably retinyl palmitate, retinol or tretinoin, ursolic acid, levulinic acid, butyl hydroxytoluene, butyl hydroxyanisole, nordihydroguaiac acid, nordihydroguaiaretic acid, trihydroxybutyrophenone, uric acid and derivatives thereof, mannose and derivatives thereof, zinc and derivatives thereof (preferably ZnO, $ZnSO_4$), selenium and derivatives thereof (preferably selenium methionine), superoxide dismutase, stilbenes and derivatives thereof (preferably stilbene oxide, trans-stilbene oxide) and the derivatives (salts, esters, ethers, sugars, nucleotides, nucleosides, peptides and lipids) of these cited active ingredients which are suitable according to the invention or extracts or fractions of plants having an antioxidant effect, preferably green tea, rooibos, honeybush, grape, rosemary, sage, melissa, thyme, lavender, olive, oats, cocoa, ginkgo, *ginseng*, liquorice, honeysuckle, *sophora, pueraria, pinus*, citrus, *Phyllanthus emblica* or St. John's wort, grape seeds, wheat germ, *Phyllanthus emblica*, coenzymes, preferably coenzyme Q10, plastoquinone and menaquinone. Preferred antioxidants are selected from the group consisting of vitamin A and derivatives, vitamin C and derivatives, tocopherol and derivatives, preferably tocopheryl acetate, and ubiquinone.

If vitamin E and/or derivatives thereof are used as the antioxidant(s), it is advantageous to choose their concentrations from the range from about 0.001 to about 10% b.w. based on the total weight of the formulation. If vitamin A or vitamin A derivatives or carotenes or derivatives thereof are used as the antioxidant(s), it is advantageous to choose their concentrations from the range from about 0.001 to about 10% b.w. based on the total weight of the formulation.

Matrix-Metalloproteinase Inhibitors (MMPI).

Preferred compositions comprise matrix-metalloproteinase inhibitors, especially those inhibiting matrix-metalloproteinases enzymatically cleaving collagen, selected from the group consisting of: ursolic acid, retinyl palmitate, propyl gallate, precocenes, 6-hydroxy-7-methoxy-2,2-dimethyl-1 (2H)-benzopyran, 3,4-dihydro-6-hydroxy-7-methoxy-2,2-dimethyl-1(2H)-benzopyran, benzamidine hydrochloride, the cysteine proteinase inhibitors N-ethylmalemide and epsilon-amino-n-caproic acid of the serinprotease inhibitors: phenylmethylsufonylfluoride, collhibin (company Pentapharm; INCI: hydrolysed rice protein), oenotherol (company Soliance; INCI: propylene glycol, aqua, *Oenothera biennis* root extract, ellagic acid and ellagitannins, for example from pomegranate), phosphoramidone hinokitiol, EDTA, galardin, EquiStat (company Collaborative Group; apple fruit extract, soya seed extract, ursolic acid, soya isoflavones and soya proteins), sage extracts, MDI (company Atrium; INCI: glycosaminoglycans), fermiskin (company Silab/Mawi; INCI: water and lentinus edodes extract), actimp 1.9.3 (company Expanscience/Rahn; INCI: hydrolysed lupine protein), lipobelle soyaglycone (company Mibelle; INCI: alcohol, polysorbate 80, lecithin and soy isoflavones), extracts from green and black tea and further plant extracts, which are listed in WO 02 069992 A1 (see tables 1-12 there, incorporated herein by reference), proteins or glycoproteins from soya, hydrolysed proteins from rice, pea or lupine, plant extracts which inhibit MMPs, preferably extracts from shitake mushrooms, extracts from the leaves of the Rosaceae family, sub-family Rosoideae, quite particularly extracts of blackberry leaf (preferably as described in WO 2005 123101 A1, incorporated herein by reference) as e.g. SymMatrix (company Symrise, INCI: Maltodextrin, *Rubus Fruticosus* (Blackberry) Leaf Extract). Preferred actives of are selected from the group consisting of retinyl palmitate, ursolic acid, extracts from the leaves of the Rosaceae family, sub-family Rosoideae, genistein and daidzein.

Skin-Moisturizing Agents.

Preferred skin moisturizing agents are selected from the group consisting of alkane diols or alkane triols comprising 3 to 12 carbon atoms, preferably $C_3$-$C_{10}$-alkane diols and $C_3$-$C_{10}$-alkane triols. More preferably the skin moisturizing agents are selected from the group consisting of: glycerol, 1,2-propylene glycol, 1,2-butylene glycol, 1,3-butylene glycol, 1,2-pentanediol, 1,2-hexanediol, 1,2-octanediol and 1,2-decanediol.

Glycosaminoglycan Stimulators.

Preferred compositions comprise substances stimulating the synthesis of glycosaminoglycans selected from the group consisting of hyaluronic acid and derivatives or salts, Subliskin (Sederma, INCI: *Sinorhizobium Meliloti* Ferment Filtrate, Cetyl Hydroxyethylcellulose, Lecithin), Hyalufix (BASF, INCI: Water, Butylene Glycol, *Alpinia galanga* leaf extract, Xanthan Gum, Caprylic/Capric Triglyceride), Stimulhyal (Soliance, INCI: Calcium ketogluconate), SynGlycan (DSM, INCI: Tetradecyl Aminobutyroylvalylaminobutyric Urea Trifluoroacetate, Glycerin, Magnesium chloride), Kalpariane (Biotech Marine), DC Upregulex (Distinctive Cosmetic Ingredients, INCI: Water, Butylene Glycol, Phospholipids, Hydrolyzed Sericin), glucosamine, N-acetyl glucosamine, retinoids, preferably retinol and vitamin A, *Arctium lappa* fruit extract, *Eriobotrya japonica* extract, Genkwanin, N-Methyl-L-serine, (−)-alpha-bisabolol or synthetic alpha-bisabolol such as e.g. Dragosantol and Dragosantol 100 from Symrise, oat glucan, *Echinacea purpurea* extract and soy protein hydrolysate. Preferred actives are selected from the group consisting of hyaluronic acid and derivatives or salts, retinol and derivatives, (−)-alpha-bisabolol or synthetic alpha-bisabolol such as e.g. Dragosantol and Dragosantol 100 from Symrise, oat glucan, *Echinacea purpurea* extract, *Sinorhizobium Meliloti* Ferment Filtrate, Calcium ketogluconate, *Alpinia galanga* leaf extract and tetradecyl aminobutyroylvalylaminobutyric urea trifluoroacetate.

Anti-Inflammatory Agents.

The compositions may also contain anti-inflammatory and/or redness and/or itch ameliorating ingredients, in particular steroidal substances of the corticosteroid type selected from the group consisting of hydrocortisone, dexamethasone, dexamethasone phosphate, methyl prednisolone or cortisone, are advantageously used as anti-inflammatory active ingredients or active ingredients to relieve reddening and itching, the list of which can be extended by the addition of other steroidal anti-inflammatories. Non-steroidal anti-inflammatories can also be used. Examples which can be cited here are oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Anthranilic acid deriva-tives, in particular avenanthramides described in WO 2004 047833 A1, are preferred anti-itch ingredients in a composition according to the present invention.

Also useful are natural or naturally occurring anti-inflammatory mixtures of substances or mixtures of substances that alleviate reddening and/or itching, in particular extracts or fractions from camomile, *Aloe vera, Commiphora* species, *Rubia* species, willow, willow-herb, oats, calendula, *arnica*, St John's wort, honeysuckle, rosemary, *Passiflora incarnata*, witch hazel, ginger or *Echinacea*; preferably selected from the group consisting of extracts or fractions from camomile, *Aloe vera*, oats, *calendula, arnica*, honeysuckle, rosemary, witch hazel, ginger or *Echinacea*, and/or pure substances, preferably alpha-bisabolol, apigenin, apigenin-7-glucoside, gingerols, shogaols, gingerdiols, dehydrogingerdiones, paradols, natural or naturally occurring avenanthramides, preferably tranilast, avenanthramide A, avenanthramide B, avenanthramide C, non-natural or non-naturally occurring avenanthramides, preferably dihydroavenanthramide D, dihydroavenanthramide E, avenanthramide D, avenan-thramide E, avenanthramide F, boswellic acid, phytosterols, glycyrrhizin, glabridin and licochalcone A; preferably selected from the group consisting of alpha-bisabolol, natural avenanthramides, non-natural avenanthramides, preferably dihydroavenanthramide D (as described in WO 2004 047833 A1), boswellic acid, phytosterols, glycyrrhizin, and licochalcone A, and/or allantoin, panthenol, lanolin, (pseudo-ceramides [preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide], glycosphingolipids, phytosterols, chitosan, mannose, lactose and β-glucans, in particular 1,3-1,4-β-glucan from oats.

When bisabolol is used in the context of the present invention it can be of natural or synthetic origin, and is preferably "alpha-bisabolol". Preferably, the bisabolol used is synthetically prepared or natural (-)-alpha-bisabolol and/or synthetic mixed-isomer alpha-bisabolol. If natural (-)-alpha-bisabolol is used, this can also be employed as a constituent of an essential oil or of a plant extract or of a fraction thereof, for example as a constituent of (fractions of) oil or extracts of camomile or of *Vanillosmopsis* (in particular *Vanillosmopsis erythropappa* or *Vanillosmopsis arborea*). Synthetic alpha-bisabolol is obtainable, for example, under the name "Dragosantol" from Symrise.

In case ginger extract is used in the context of the present invention, preferably extracts of the fresh or dried ginger root are used which are prepared by extraction with methanol, ethanol, iso-propanol, acetone, ethyl acetate, carbon dioxide (CO2), hexane, methylene chloride, chloroform or other solvents or solvent mixtures of comparable polarity. The extracts are characterized by the presence of active skin irritation-reducing amounts of constituents such as e.g. gingerols, shogaols, gingerdiols, dehydrogingerdiones and/or paradols.

TRPV1 Antagonists.

Suitable compounds which reduce the hypersensitivity of skin nerves based on their action as TRPV1 antagonists, encompass e.g. trans-4-tert-butyl cyclohexanol as described in WO 2009 087242 A1, or indirect modulators of TRPV1 by an activation of the μ-receptor, e.g. acetyl tetrapeptide-15, are preferred.

Desquamating Agents.

The compositions may also contain desquamating agents (component b5) in amounts of about 0.1 to about 30% b.w. preferably about 0.5 to about 15% b.w., particularly preferably about 1 to about 10% b.w. based on the total weight of the preparation. The expression "desquamating agent" is understood to mean any compound capable of acting:

either directly on desquamation by promoting exfoliation, such as β-hydroxy acids, in particular salicylic acid and its derivatives (including 5-n-octanoylsalicylic acid); α-hydroxy acids, such as glycolic, citric, lactic, tartaric, malic or mandelic acids; urea; gentisic acid; oligofucoses; cinnamic acid; extract of *Sophora japonica*; resveratrol and some derivatives of jasmonic acid;

or on the enzymes involved in the desquamation or the degradation of the corneodesmosomes, glycosidases, stratum corneum chymotryptic enzyme (SCCE) or other proteases (trypsin, chymotrypsin-like). There may be mentioned agents chelating inorganic salts: EDTA; N-acyl-N,N',N'-ethylenediaminetriacetic acid; aminosulphonic compounds and in particular (N-2-hydroxyethylpiperazine-N-2-ethane)sulphonic acid (HEPES); derivatives of 2-oxothiazolidine-4-carboxylic acid (procysteine); derivatives of alpha-amino acids of the glycine type (as described in EP-0 852 949, and sodium methylglycine diacetate marketed by BASF under the trade name TRILON M); honey; sugar derivatives such as O-octanoyl-6-D-maltose and N-acetylglucosamine; chestnut extracts such as those marketed by the company SILAB under the name Recoverine®, prickly pear extracts such as those marketed under the name Exfolactive® by the company SILAB, or Phytosphingosine SLC® (phytosphingosine grafted with a salicylic acid) marketed by the company Degussa.

Desquamating agents suitable for the invention may be chosen in particular from the group comprising sulphonic acids, calcium chelators, α-hydroxy acids such as glycolic, citric, lactic, tartaric, malic or mandelic acids; ascorbic acid and its derivatives such as ascorbyl glucoside and magnesium ascorbyl phosphate; nicotinamide; urea; (N-2-hydroxyethylpiperazine-N-2-ethane)sulphonic acid (HEPES), (β-hydroxy acids such as salicylic acid and its derivatives, retinoids such as retinol and its esters, retinal, retinoic acid and its derivatives, those described in the documents FR 2570377 A1, EP 0199636 A1, EP 0325540 A1, EP 0402072 A1, chestnut or prickly pear extracts, in particular marketed by SILAB; reducing compounds such as cysteine or cysteine precursors.

Desquamating agents which can be used are also nicotinic acid and its esters and nicotinamide, also called vitamin B3 or vitamin PP, and ascorbic acid and its precursors, as described in particular in application EP 1529522 A1.

Anti-Cellulite Agents.

Anti-cellulite agents and lipolytic agents are preferably selected from the group consisting of those described in WO 2007/077541, and beta-adrenergic receptor agonists such as synephrine and its derivatives, and cyclohexyl carbamates described in WO 2010/097479. Agents enhancing or boosting the activity of anti-cellulite agents, in particular agents which stimulate and/or depolarise C nerve fibres, are preferably selected from the group consisting of capsaicin and derivatives thereof, vanillyl-nonylamid and derivatives thereof, L-carnitine, coenzym A, isoflavonoides, soy extracts, *ananas* extract and conjugated linoleic acid.

Fat enhancing agents. Formulations and products according to the present invention may also comprise one or more fat enhancing and/or adipogenic agents as well as agents enhancing or boosting the activity of fat enhancing agents. A fat enhancing agent is for example hydroxymethoxyphenyl propylmethylmethoxybenzofuran (trade name: Sym3D®).

Hair Growth Activators or Inhibitors

Formulations and products according to the present invention may also comprise one or more hair growth activators, i.e. agents to stimulate hair growth. Hair growth activators are preferably selected from the group consisting of pyrimidine derivatives such as 2,4-diaminopyrimidine-3-oxide (Aminexil), 2,4-diamino-6-piperidinopyrimidine-3-oxide (Minoxidil) and derivatives thereof, 6-amino-1,2-dihydro-1-hydroxy-2-imino-4-piperidinopyrimidine and its derivatives, xanthine alkaloids such as caffeine, theobromine and theophylline and derivatives thereof, quercetin and derivatives, dihydroquercetin (taxifolin) and derivatives, potassium channel openers, antiandrogenic agents, synthetic or natural 5-reductase inhibitors, nicotinic acid esters such as tocopheryl nicotinate, benzyl nicotinate and C1-C6 alkyl nicotinate, proteins such as for example the tripeptide Lys-Pro-Val, diphencypren, hormons, finasteride, dutasteride, flutamide, bicalutamide, pregnane deriva-tives, progesterone and its derivatives, cyproterone acetate, spironolactone and other diuretics, calcineurin inhibitors such as FK506 (Tacrolimus, Fujimycin) and its derivatives, Cyclosporin A and derivatives thereof, zinc and zinc salts, polyphenols, procyanidins, proanthocyanidins, phytosterols such as for example beta-sitosterol, biotin, eugenol, (±)-beta-citronellol, panthenol, glycogen for example from mussels, extracts from microorganisms, algae, plants and plant parts of for example the genera *dandelion* (*Leontodon* or *Taraxacum*), *Orthosiphon, Vitex, Coffea, Paullinia, Theobroma, Asiasarum, Cucurbita* or *Styphnolobium, Serenoa repens* (saw palmetto), *Sophora flavescens, Pygeum africanum, Panicum miliaceum, Cimicifuga racemosa, Glycine max, Eugenia caryophyllata, Cotinus coggygria, Hibiscus rosa-sinensis, Camellia sinensis, Ilex paraguariensis, Isochrysis galbana*, licorice, grape, apple, barley or hops or/nd hydrolysates from rice or wheat.

Alternatively, formulations and products according to the present invention may comprise one or more hair growth inhibitors (as described above), i.e. agents to reduce or prevent hair growth. Hair growth inhibitors are preferably selected from the group consisting of activin, activin derivatives or activin agonists, ornithine decarboxylase inhibitors such as alpha-difluoromethylornithine or pentacyclic triterpenes like for example ursolic acid, betulin, betulinic acid, oleanolic acid and derivatives thereof, 5alpha-reductase inhibitors, androgen receptor antagonists, S-adenosylmethionine decarboxylase inhibitors, gamma-glutamyl transpeptidase inhibitors, transglutaminase inhibitors, soybean-derived serine protease inhibitors, extracts from microorganisms, algae, different microalgae or plants and plant parts of for example the families Leguminosae, Solanaceae, Graminae, Asclepiadaceae or Cucurbitaceae, the genera *Chondrus, Gloiopeltis, Ceramium, Durvillea, Glycine max, Sanguisorba officinalis, Calendula officinalis, Hamamelis virginiana, Arnica montana, Salix alba, Hypericum perforatum* or *Gymnenna sylvestre*.

Cooling Agents

The compositions may also contain one or more substances with a physiological cooling effect (cooling agents), which are preferably selected here from the following list: menthol and menthol derivatives (for example L-menthol, D-menthol, racemic menthol, isomenthol, neoisomenthol, neomenthol) menthylethers (for example (I-menthoxy)-1,2-propandiol, (I-menthoxy)-2-methyl-1,2-propandiol, 1-menthyl-methylether), menthylesters (for example menthylformiate, menthylacetate, menthylisobutyrate, menthyllactates, L-menthyl-L-lactate, L-menthyl-D-lactate, menthyl-(2-methoxy)acetate, menthyl-(2-methoxyethoxy) acetate, menthylpyroglutamate), menthylcarbonates (for example menthylpropyleneglycolcarbonate, menthylethyleneglycolcarbonate, menthylglycerolcarbonate or mixtures thereof), the semi-esters of menthols with a dicarboxylic acid or derivatives thereof (for example mono-menthylsuccinate, monomenthylglutarate, mono-menthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or $N^{\alpha}$-(menthanecarbonyl)glycinethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005 049553 A1, methanecarboxylic acid-N-(alkoxyalkyl)amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide [WS23]), isopulegol or its esters (I-(−)-isopulegol, I-(−) isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840), further carboxamides (for example N-(2-(pyridin-2-yl)ethyl)-3-p-menthanecarboxamide or related compounds), (1R,2S,5R)—N-(4-Methoxyphenyl)-5-methyl-2-(1-isopropyl)cyclohexane-carboxamide [WS12], oxamates (preferably those described in EP 2033688 A2).

Anti-Microbial Agents

Suitable anti-microbial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylenebis(6-bromo-4-chlorophenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen CAT). The substances inhibit enzyme activity, thereby reducing the formation of odour. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Odour Absorbers and Antiperspirant Active Agents

Suitable odour absorbers are substances which are able to absorb and largely retain odour-forming compounds. They lower the partial pressure of the individual components, thus also reducing their rate of diffusion. It is important that perfumes must remain unimpaired in this process. Odour absorbers are not effective against bacteria. They comprise, for example, as main constituent, a complex zinc salt of ricinoleic acid or specific, largely odour-neutral fragrances which are known to the person skilled in the art as "fixatives", such as, for example, extracts of labdanum or styrax or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal products, such as, for example, civet and castoreum. Typical synthetic fragrance compounds are products of the ester, ether, aldehyde, ketone, alcohol, and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linaool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniperberry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine.

Film Formers and Anti-Dandruff Agents

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Carriers and Hydrotropes

Preferred cosmetics carrier materials are solid or liquid at 25° C. and 1013 mbar (including highly viscous substances) as for example glycerol, 1,2-propylene glycol, 1,2-butylene glycol, 1,3-propylene glycol, 1,3-butylene glycol, ethanol, water and mixtures of two or more of said liquid carrier materials with water. Optionally, these preparations according to the invention may be produced using preservatives or solubilizers. Other preferred liquid carrier substances, which may be a component of a preparation according to the invention are selected from the group consisting of oils such as vegetable oil, neutral oil and mineral oil.

Preferred solid carrier materials, which may be a component of a preparation according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gellan gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose.

In addition, hydrotropes, for example ethanol, isopropyl alcohol or polyols, may be used to improve flow behavior. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 Dalton;

technical oligoglycerol mixtures with a degree of self-condensation of 1.5 to 10, such as for example technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

Perfume Oils and Fragrances

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, ?-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. Advantageous coloured pigments are for example titanium dioxide, mica, iron oxides (e.g. $Fe_2O_3$ $Fe_3O_4$, FeO (OH)) and/or tin oxide. Advantageous dyes are for example carmine, Berlin blue, chromium oxide green, ultramarine blue and/or manganese violet.

Preparations

Preferred compositions according to the present inventions are selected from the group of products for treatment, protecting, care and cleansing of the skin and/or hair or as a make-up product, preferably as a leave-on product (meaning that the one or more compounds of formula (I) stay on the skin and/or hair for a longer period of time, compared to rinse-off products, so that the moisturizing and/or anti-ageing and/or wound healing promoting action thereof is more pronounced).

The formulations according to the invention are preferably in the form of an emulsion, e.g. W/O (water-in-oil), O/W (oil-in-water), W/O/W (water-in-oil-in-water), O/W/O (oil-in-water-in-oil) emulsion, PIT emulsion, Pickering emulsion, emulsion with a low oil content, micro- or nanoemulsion, a solution, e.g. in oil (fatty oils or fatty acid esters, in particular $C_6$-$C_{32}$ fatty acid $C_2$-$C_{30}$ esters) or silicone oil, dispersion, suspension, creme, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), a mask, a pencil, stick, roll-on, pump, aerosol (foaming, nonfoaming or post-foaming), a deodorant and/or antiperspirant, mouthwash and mouth rinse, a foot care product (including keratolytic, deodorant), an insect repellent, a sunscreen, aftersun preparation, a shaving product, aftershave balm, pre- and aftershave lotion, a depilatory agent, a hair care product such as e.g. shampoo (including 2-in-1 shampoo, antidandruff shampoo, baby shampoo, shampoo for dry scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

The formulations according to the invention are particularly preferably in the form of an emulsion, in particular in the form of a W/O, O/W, W/O/W, O/W/O emulsion, PIT emulsion, Pickering emulsion, emulsion with a low oil content, micro- or nanoemulsion, a gel (including hydrogel, hydrodispersion gel, oleogel), a solution e.g. in oil (fatty oils or fatty acid esters, in particular $C_6$-$C_{32}$ fatty acid $C_2$-$C_{30}$ esters)) or silicone oil, or a spray (e.g. pump spray or spray with propellant).

Auxiliary substances and additives can be included in quantities of 5 to 99% b.w., preferably 10 to 80% b.w., based on the total weight of the formulation. The amounts of cosmetic or dermatological auxiliary agents and additives and perfume to be used in each case can easily be determined by the person skilled in the art by simple trial and error, depending on the nature of the particular product.

The preparations can also contain water in a quantity of up to 99% b.w., preferably 5 to 80% b.w., based on the total weight of the preparation.

INDUSTRIAL APPLICATION

The present invention also encompasses the following embodiments:
(i) A method for improving the antimicrobial performance of a cosmetic or personal care composition by incorporating a working amount of the aforesaid antimicrobial composition, which is preferably added in an amount of about 0.05 to about 2% b.w., more preferably in an amount of 0.1 to 1.5% b.w. and most preferred in an amount of about 0.75 to about 1% b.w.; and
(ii) The use of the aforesaid antimicrobial composition for improving the antimicrobial performance of a cosmetic or a personal care composition, said antimicrobial composition preferably added in an amount of about 0.05 to about 2% b.w., more preferably in an amount of 0.1 to 1.5% b.w. and most preferred in an amount of about 0.75 to about 1% b.w.

EXAMPLES

Synergistic Antimicrobial Flavour and Fragrance Compositions

Synergistic antimicrobial activity of lactate esters and other flavor and fragrance ingredients against different microorganisms relevant for cosmetics were investigated.

To calculate the synergism between lactate esters and other flavor and fragrance ingredients, the Kull equation[1,2] was used

[1] Kull, F. C., Eismann, P. C., Sylvestrowicz, H. D., and R. L. Mayer (1961). Mixtures of Quaternary Ammonium Compounds and Long-chain Fatty Acids as Antifungal Agents. Applied Microbiology 9, 538-541.
[2] Steinberg, D. C. (2000). Measuring Synergy. Cosmetics & Toiletries 115 (11), 59-62.

$$SI = (C_{mixture} \times P_A)/C_A + (C_{mixture} \times P_B)/C_B$$

where
SI is the Synergy Index according to Kull[1,2]
$C_A$ is the cell count for substance A
$C_B$ is the cell count for substance B
$C_{mixture}$ is the cell count for the mixture of substances A and B
$P_A$ is the proportion of the substance A in the mixture
$P_B$ is the proportion of the substance B in the mixture.

Colony counts of <10 were arbitrarily set to 10, in order to allow for synergy calculations with the above equation. The abbreviation "n.a." means not applicable.

Example 1

The results for butyl lactate (BuL) and p-anisic aldehyde (AAld) against the mould *A. brasiliensis* are shown in Table A.

TABLE A

Synergistic activity of butyl lactate and p-anisic aldehyde

|  | day 0 | day 2 | day 7 | day 14 | day 28 |
|---|---|---|---|---|---|
| Colony counts (cfu/g formulation) | | | | | |
| 1.25% BuL | 2.900.000 | 730.000 | 1.600.000 | 1.100.000 | 150.000 |
| 0.5% AAld | 2.900.000 | 560.000 | 140.000 | 2.100 | 15 |
| 1% BuL + 0.25% AAld | 2.900.000 | 350.000 | 30 | 10 | 10 |
| Relative colony counts | | | | | |
| 1.25% BuL | 1.0000 | 0.2517 | 0.5517 | 0.3793 | 0.0517 |
| 0.5% AAld | 1.0000 | 0.1931 | 0.0483 | 0.0007 | 0.0000 |
| 1% BuL + 0.25% AAld | 1.0000 | 0.1207 | 0.0000 | 0.0000 | 0.0000 |
| Synergy Index SI | n.a. | 0.6961 | 0.0001 | 0.0024 | 0.3334 |

The Synergy Index SI for the combination of butyl lactate and p-anisic aldehyde against *A. brasiliensis*, calculated according to Kull's equation (I), is 0.0001, 0.0024, and 0.3334 for the time points day 7, 14, and 28, respectively, indicating a very strong synergism between these two compounds.

Example 2

The results for butyl lactate (BuL) and 3-phenylpropanol (PP) against the yeast *C. albicans* are shown in Table B.

TABLE B

Synergistic activity of butyl lactate and 3-phenylpropanol

|  | day 0 | day 2 | day 7 | day 14 | day 28 |
|---|---|---|---|---|---|
| Colony counts (cfu/g formulation) | | | | | |
| 1.25% BuL | 2.400.000 | 740.000 | 430 | 10 | 10 |
| 0.5% PP | 2.400.000 | 1.100.000 | 930.000 | 31.000 | 10 |
| 1% BuL + 0.25% PP | 2.400.000 | 670.000 | 10 | 10 | 10 |
| Relative colony counts | | | | | |
| 1.25% BuL | 1.0000 | 0.3083 | 0.0002 | 0.0000 | 0.0000 |
| 0.5% PP | 1.0000 | 0.4583 | 0.3875 | 0.0129 | 0.0000 |
| 1% BuL + 0.25% PP | 1.0000 | 0.2792 | 0.0000 | 0.0000 | 0.0000 |
| Synergy Index SI | n.a. | 1.0289 | 0.0186 | 0.8002 | 1.3000[1] |

[1] all values below detection limit

The Synergy Index SI for the combination of butyl lactate and 3-phenylpropanol against *C. albicans*, calculated according to Kull's equation (I), is 0.0186 for the time point day 7, indicating a very strong synergism between these two compounds.

Example 3

The results for butyl lactate (BuL) and p-anisic acid (AAc) against the gram negative bacterium *E. coli* are shown in Table C.

TABLE C

Synergistic activity of butyl lactate and p-anisic acid

|  | day 0 | day 2 | day 7 | day 14 | day 28 |
|---|---|---|---|---|---|
|  | Colony counts (cfu/g formulation) | | | | |
| 1.25% BuL | 3.200.000 | 13.000 | 10 | 10 | 10 |
| 0.5% AAc | 2.300.000 | 140.000 | 15.000 | 3.100 | 10 |
| 1% BuL + 0.25% AAc | 2.300.000 | 10 | 10 | 10 | 10 |
|  | Relative colony counts | | | | |
| 1.25% BuL | 1.0000 | 0.0041 | 0.0000 | 0.0000 | 0.0000 |
| 0.5% AAc | 1.0000 | 0.0609 | 0.0065 | 0.0013 | 0.0000 |
| 1% BuL + 0.25% AAc | 1.0000 | 0.0000 | 0.0000 | 0.0000 | 0.0000 |
| Synergy Index SI | n.a. | 0.0009 | 1.1134 | 1.1147 | 1.6130[1)] | all values below detection limit

The Synergy Index SI for the combination of butyl lactate and p-anisic acid against *E. coli*, calculated according to Kull's equation (I), is 0.0009 for the time point day 2, indicating a very strong synergism between these two compounds.

Example 4

The results for amyl lactate (AL) and p-anisic aldehyde (AAld) against the mould *A. brasiliensis* are shown in Table D.

TABLE D

Synergistic activity of amyl lactate and p-anisic aldehyde

|  | day 0 | day 2 | day 7 | day 14 | day 28 |
|---|---|---|---|---|---|
|  | Colony counts (cfu/g formulation) | | | | |
| 1% AL | 2.900.000 | 160.000 | 1.400.000 | 320.000 | 660 |
| 0.5% AAld | 2.900.000 | 560.000 | 140.000 | 2.100 | 15 |
| 0.75% AL + 0.25% AAld | 2.900.000 | 230.000 | 1.700 | 10 | 10 |
|  | Relative colony counts | | | | |
| 1% AL | 1.0000 | 0.0552 | 0.4828 | 0.1103 | 0.0002 |
| 0.5% AAld | 1.0000 | 0.1931 | 0.0483 | 0.0007 | 0.0000 |
| 0.75% AL + 0.25% AAld | 1.0000 | 0.0793 | 0.0006 | 0.0000 | 0.0000 |
| Synergy Index SI | n.a. | 1.2835 | 0.0070 | 0.0024 | 0.3447 |

The Synergy Index SI for the combination of amyl lactate and p-anisic aldehyde against *A. brasiliensis*, calculated according to Kull's equation (I), is 0.0070, 0.0024, and 0.3447 for the time points day 7, 14, and 28, respectively, indicating a very strong synergism between these two compounds.

Example 5

The results for amyl lactate (AL) and 3-phenylpropanol (PP) against the gram positive bacterium *S. aureus* are shown in Table E.

TABLE E

Synergistic activity of amyl lactate and 3-phenylpropanol

|  | day 0 | day 2 | day 7 | day 14 | day 28 |
|---|---|---|---|---|---|
|  | Colony counts (cfu/g formulation) | | | | |
| 1% AL | 2.900.000 | 21.000 | 15 | 10 | 10 |
| 0.5% PP | 2.900.000 | 23.000 | 80 | 10 | 10 |
| 0.75% AL + 0.25% PP | 2.900.000 | 10 | 10 | 10 | 10 |
|  | Relative colony counts | | | | |
| 1% AL | 1.0000 | 0.0072 | 0.0000 | 0.0000 | 0.0000 |
| 0.5% PP | 1.0000 | 0.0079 | 0.0000 | 0.0000 | 0.0000 |
| 0.75% AL + 0.25% PP | 1.0000 | 0.0000 | 0.0000 | 0.0000 | 0.0000 |
| Synergy Index SI | n.a. | 0.0006 | 0.5625 | 1.2500[1)] | 1.2500[1)] | all values below detection limit

The Synergy Index SI for the combination of amyl lactate and 3-phenylpropanol against *S. aureus*, calculated according to Kull's equation (I), is 0.0006, and 0.5625 for the time points day 2 and 7, respectively, indicating a very strong synergism between these two compounds.

Example 6

The results for amyl lactate (AL) and p-anisic acid (AAc) against the gram positive bacterium *S. aureus* are shown in Table F.

TABLE F

Synergistic activity of amyl lactate and p-anisic acid

|  | day 0 | day 2 | day 7 | day 14 | day 28 |
|---|---|---|---|---|---|
|  | Colony counts (cfu/g formulation) | | | | |
| 1% AL | 2.900.000 | 21.000 | 15 | 10 | 10 |
| 0.5% AAc | 2.100.000 | 1.700.000 | 130 | 10 | 10 |
| 0.75% AL + 0.25% AAc | 2.100.000 | 10 | 10 | 10 | 10 |
|  | Relative colony counts | | | | |
| 1% AL | 1.0000 | 0.0072 | 0.0000 | 0.0000 | 0.0000 |
| 0.5% AAc | 1.0000 | 0.8095 | 0.0001 | 0.0000 | 0.0000 |
| 0.75% AL + 0.25% AAc | 1.0000 | 0.0000 | 0.0000 | 0.0000 | 0.0000 |
| Synergy Index SI | n.a. | 0.0005 | 0.7289 | 1.5357[1)] | 1.5357[1)] |

[1)] all values below detection limit

The Synergy Index SI for the combination of amyl lactate and p-anisic acid against *S. aureus*, calculated according to Kull's equation (I), is 0.0005 for the time point day 2, indicating a very strong synergism between these two compounds.

Example 7

The results for benzyl lactate (AL) and p-anisic aldehyde (AAld) against the mould *A. brasiliensis* are shown in Table G.

TABLE G

Synergistic activity of benzyl lactate and p-anisic aldehyde

|  | day 0 | day 2 | day 7 | day 14 | day 28 |
|---|---|---|---|---|---|
|  | Colony counts (cfu/g formulation) | | | | |
| 1% BL | 2.900.000 | 270.000 | 4.500 | 110 | 10 |
| 0.5% AAld | 2.900.000 | 560.000 | 140.000 | 2.100 | 15 |

TABLE G-continued

Synergistic activity of benzyl lactate and p-anisic aldehyde

|  | day 0 | day 2 | day 7 | day 14 | day 28 |
|---|---|---|---|---|---|
| 0.75% BL + 0.25% AAld | 2.900.000 | 41.000 | 10 | 10 | 10 |
|  | Relative colony counts | | | | |
| 1% BL | 1.0000 | 0.0931 | 0.0016 | 0.0000 | 0.0000 |
| 0.5% AAld | 1.0000 | 0.1931 | 0.0483 | 0.0007 | 0.0000 |
| 0.75% BL + 0.25% AAld | 1.0000 | 0.0141 | 0.0000 | 0.0000 | 0.0000 |
| Synergy Index SI | n.a. | 0.1505 | 0.0017 | 0.0706 | 1.0833 |

The Synergy Index SI for the combination of benzyl lactate and p-anisic aldehyde against *A. brasiliensis*, calculated according to Kull's equation (I), is 0.1505, 0.0017, and 0.0706 for the time points day 2, 7, and 14, respectively, indicating a very strong synergism between these two compounds.

Example 8

The results for benzyl lactate (AL) and 3-phenylpropanol (PP) against the gram positive bacterium *S. aureus* are shown in Table H.

TABLE H

Synergistic activity of benzyl lactate and 3-phenylpropanol

|  | day 0 | day 2 | day 7 | day 14 | day 28 |
|---|---|---|---|---|---|
|  | Colony counts (cfu/g formulation) | | | | |
| 1% BL | 2.900.000 | 1.600 | 10 | 10 | 10 |
| 0.5% PP | 2.900.000 | 23.000 | 80 | 10 | 10 |
| 0.75% BL + 0.25% PP | 2.900.000 | 10 | 10 | 10 | 10 |
|  | Relative colony counts | | | | |
| 1% BL | 1.0000 | 0.0006 | 0.0000 | 0.0000 | 0.0000 |
| 0.5% PP | 1.0000 | 0.0079 | 0.0000 | 0.0000 | 0.0000 |
| 0.75% BL + 0.25% PP | 1.0000 | 0.0000 | 0.0000 | 0.0000 | 0.0000 |
| Synergy Index SI | n.a. | 0.0049 | 0.8125 | 1.2500[1] | 1.2500[1] |

[1] all values below detection limit

The Synergy Index SI for the combination of benzyl lactate and 3-phenylpropanol against *S. aureus*, calculated according to Kull's equation (I), is 0.0049 for the time point day 2, indicating a very strong synergism between these two compounds.

Example 9

The results for benzyl lactate (AL) and p-anisic acid (AAc) against the mould *A. brasiliensis* are shown in Table J.

TABLE J

Synergistic activity of benzyl lactate and p-anisic acid

|  | day 0 | day 2 | day 7 | day 14 | day 28 |
|---|---|---|---|---|---|
|  | Colony counts (cfu/g formulation) | | | | |
| 1% BL | 2.900.000 | 270.000 | 4.500 | 110 | 10 |
| 0.5% AAc | 3.700.000 | 1.300.000 | 200.000 | 1.200.000 | 2.100.000 |
| 0.75% BL + 0.25% AAc | 2.900.000 | 41.000 | 10 | 10 | 10 |

TABLE J-continued

Synergistic activity of benzyl lactate and p-anisic acid

|  | day 0 | day 2 | day 7 | day 14 | day 28 |
|---|---|---|---|---|---|
|  | Relative colony counts | | | | |
| 1% BL | 1.0000 | 0.0931 | 0.0016 | 0.0000 | 0.0000 |
| 0.5% AAc | 1.0000 | 0.3514 | 0.0541 | 0.3243 | 0.5676 |
| 0.75% BL + 0.25% AAc | 1.0000 | 0.0141 | 0.0000 | 0.0000 | 0.0000 |
| Synergy Index SI | n.a. | 0.0384 | 0.7322 | 0.3100 | 0.5878 |

The Synergy Index SI for the combination of benzyl lactate and p-anisic acid against *A. brasiliensis*, calculated according to Kull's equation (I), is 0.0384, 0.3100, and 0.5878 for the time point day 2, 14, and 28, respectively, indicating a very strong synergism between these two compounds.

Formulation Examples

TABLE 1

Perfume oil P1 (Amounts in ‰ b.w.)

| Ingredients | Amount |
|---|---|
| AMBRETTOLIDE (MACRO) | 10.00 |
| AMBROXIDE 10% in IPM | 10.00 |
| BENZYL ACETATE | 20.00 |
| BENZYL SALICYLATE | 15.00 |
| BERGAMOT OIL. bergapten-free | 60.00 |
| CALONE ® 1951 10% in DPG | 15.00 |
| COUMARIN | 5.00 |
| CYCLOGALBANATE ® 10% in DPG | 10.00 |
| ALPHA-DAMASCONE 1% in DPG | 20.00 |
| DIHYDROMYRCENOL | 10.00 |
| ETHYL LINALOOL | 75.00 |
| ETHYL LINALYLACETATE | 50.00 |
| ETHYL MALTOL 1% in DEP | 10.00 |
| ETHYLENE BRASSYLATE (MACRO) | 80.00 |
| FLOROSA | 40.00 |
| GERANYLACETATE | 10.00 |
| HEDIONE ® HC/30 | 35.00 |
| HEDIONE ® | 210.00 |
| HELIONAL ® | 15.00 |
| HELVETOLIDE ® (ALICYC) | 30.00 |
| HEXENYLSALICYLATE CIS-3 | 20.00 |
| ISO E SUPER ® | 40.00 |
| LEAFOVERT ® 10% in DEP | 10.00 |
| LILIAL ® | 80.00 |
| LYRAL ® | 20.00 |
| MANDARIN OIL | 10.00 |
| STYRALYL ACETATE | 5.00 |
| SYMROSE ® | 15.00 |
| VANILLIN 10% in DEP | 20.00 |
| DIPROPYLENE GLYCOL (DPG) | 50.00 |
| TOTAL: | 1,000.00 |

TABLE 2

Perfume oil P2 (Amounts in ‰ b.w.)

| Ingredients | Amount |
|---|---|
| AMAROCITE ® | 10.00 |
| AMBROCENIDE ® 10% in DPG | 5.00 |
| AMBROXIDE | 15.00 |
| AURELIONE ® (7/8-Cyclohexadecenone) (MACRO) | 70.00 |
| BERGAMOT OIL. bergapten-free | 90.00 |
| CALONE ® 1951 10% in DPG | 20.00 |
| CARAWAY OIL | 10.00 |

TABLE 2-continued

Perfume oil P2 (Amounts in ‰ b.w.)

| Ingredients | Amount |
|---|---|
| CITRAL | 20.00 |
| COUMARIN | 10.00 |
| ALPHA-DAMASCONE 1% in DPG | 15.00 |
| DIHYDROMYRCENOL | 70.00 |
| ESTRAGON OIL | 10.00 |
| ETHYL LINALOOL | 100.00 |
| ETHYL LINALYLACETATE | 90.00 |
| EUGENOL | 10.00 |
| EVERNYL ® | 5.00 |
| FRUCTATE ® | 5.00 |
| GERANIUM OIL | 5.00 |
| HEDIONE ® HC/30 | 100.00 |
| HELIONAL ® | 10.00 |
| INDOLE 10% in DPG | 5.00 |
| ISO E SUPER ® | 100.00 |
| KEPHALIS ® | 5.00 |
| LAVENDER OIL | 40.00 |
| CITRUS OIL | 80.00 |
| LILIAL ® | 30.00 |
| MANDARIN OIL | 20.00 |
| MUSCENONE (MACRO) | 5.00 |
| SANDRANOL ® | 10.00 |
| VANILLIN 10% in DPG | 5.00 |
| DIPROPYLENE GLYCOL | 30.00 |
| TOTAL: | 1,000.00 |

TABLE 3

Perfume oil P3 (Amounts in ‰ b.w.)

| Ingredients | Amount |
|---|---|
| ALDEHYDE C10 (n-decanal) 10% in DPG | 20.00 |
| ALDEHYDE C11 (n-undecanal) 10% in DPG | 5.00 |
| ALDEHYDE C12 (n-dodecanal) 10% in DPG | 15.00 |
| AMBRETTOLIDE (MACRO) | 5.00 |
| AMBROCENIDE ® 1% in DPG | 20.00 |
| AURELIONE ® (MACRO) | 30.00 |
| BENZYL ACETATE | 30.00 |
| CITRONELLA OIL | 15.00 |
| ETHYL VANILLIN 1% in DPG | 20.00 |
| ETHYLENE BRASSYLATE (MACRO) | 70.00 |
| FRUCTATE ® 10% in DPG | 20.00 |
| GERANYL ACETATE | 10.00 |
| GLOBALIDE ® (MACRO) | 30.00 |
| HEDIONE ® | 30.00 |
| ALPHA-HEXYLCINNAMALDEHYDE | 90.00 |
| INDOLE 10% in DPG | 5.00 |
| ISO E SUPER ® | 120.00 |
| KEPHALIS ® | 5.00 |
| LINALOOL | 150.00 |
| LINALYL ACETATE | 60.00 |
| BETA-METHYLNAPHTYLKETONE | 5.00 |
| NEROLIDOL | 20.00 |
| NEROLIONE 10% in DPG | 20.00 |
| BRAZILIAN ORANGE OIL | 100.00 |
| PHENYLETHYL ACETATE | 5.00 |
| PHENYLETHYL ALCOHOL | 30.00 |
| TERPINEOL | 20.00 |
| DIPROPYLENE GLYCOL | 50.00 |
| TOTAL: | 1,000.00 |

TABLE 4

Perfume oil P4 with white blossom smell (Amounts in ‰ b.w.)

| Ingredients | Amount |
|---|---|
| Benzylacetate | 60.00 |
| Citronellylacetate | 60.00 |
| Cyclamene aldehyde (2-methyl-3-(4-isopropylphenyl) propanal | 20.00 |
| Dipropylene glycol | 60.00 |
| Ethyllinalool | 40.00 |
| Florol (2-isobutyl-4-methyltetrahydro-2H-pyran-4-ol) | 30.00 |
| Globanone [(E/Z)-8-cyclohexadecen-1-one] | 180.00 |
| Hedione (methyldihydrojasmonate) | 140.00 |
| Hexenylsalicylate. cis-3 | 10.00 |
| Vertocitral (2.4-dimethyl-3-cyclohexenecarboxaldehyde) | 5.00 |
| Hydratropaaldehyde. 10% in DPG | 5.00 |
| Isodamascone (1-(2.4.4-trimethyl-2-cyclohexen-1-yl)-2-buten-1-one. 10% in DPG | 5.00 |
| Isomuscone (cyclohexadecanone) | 40.00 |
| Jacinthaflor (2-methyl-4-phenyl-1.3-dioxolane) | 10.00 |
| Cis-jasmone. 10% in DPG | 20.00 |
| Linalool | 50.00 |
| Linalylacetate | 30.00 |
| Methylbenzoate. 10% in DPG | 25.00 |
| para-methyl cresol. 10% in DPG | 10.00 |
| Nerol | 20.00 |
| Phenylpropylaldehyde | 5.00 |
| 2-Phenylethyl alcohol | 82.00 |
| Tetrahydrogeraniol | 13.00 |
| 2.2-dimethyl-3-cyclohexyl-1-propanol | 80.00 |
| Total: | 1,000.00 |

The perfume oils P1. P2. P3 and P4 from the above examples were worked separately in each case into the here presented formulations.

TABLE 5

Liquid soap, transparent (Amounts in % b.w.)

| Ingredients | INCI Name | Amount |
|---|---|---|
| Tagat O 2 | PEG-20 Glyceryl Oleate | 2.5 |
| Coconut oil diethanolamine condensate | Cocamide DEA | 5.0 |
| Abil B 8842 | Cyclomethicone | 0.5 |
| Sodium laurylethersulfate. 28% | Sodium Laureth Sulfate | 35.0 |
| Tego-Betaine L7 | Cocamidopropyl Betaine | 5.0 |
| Soap. 25% | Coconut acid. Potassium salt. Potassium Oleate | 20.0 |
| Perfume oil P1. P2. P3 or P4 | Fragrance | 0.4 |
| Preservative | DMDM Hydantoin | 0.1 |
| Butyl lactate | | 0.5 |
| p-Anisic aldehyde | | 0.1 |
| Water | Water | Ad 100 |

TABLE 6

Syndet soap. liquid (Amounts in % b.w.)

| Ingredients | INCI Name | Amount |
|---|---|---|
| Elfan OS 46 | Sodium Olefin C14-C16 Sulfonate | 35.5 |
| Armoteric LB | Lauryl Betaine | 8.0 |
| Elfan SG | | 10.0 |
| Elfacos GT 282 L | Talloweth-60 Myristyl Glycol | 3.0 |
| PCL-Liquid 100 | Cetearyl Ethylhexanoate | 4.0 |
| Perfume oil P1. P2. P3 or P4 | Fragrance | 0.4 |
| Preservative | Methylchloroisothiazolinone. | 0.05 |
| 4-Hydroxyacetophenone | Hydroxyacetophenone | 0.4 |
| Butyl lactate | | 0.3 |
| Propyl lactate | | 0.4 |
| 3-Phenylpropanol | | 0.1 |
| Water | Water | Ad 100 |

TABLE 7

Cosmetic lotion for body wash (Amounts in % b.w.)

| Ingredients | INCI Name | Amount |
|---|---|---|
| Lumerol K 28 | Disodium Laureth Sulfosuccinate. Cocamidopropyl Betaine. Magnesium Lauryl Sulfate | 33.0 |
| Amphotensid B 4 | Cocamidopropyl Betaine | 10.0 |
| Perlglanzmittel GM 4055 | MIPA-Pareth-25 Sulfate. Glycol Stearate | 4.0 |
| Sodium Chloride | Sodium Chloride | 2.0 |
| Avocado oil | *Persea Gratissima* (Avocado) Oil | 3.0 |
| Water | Water | Ad 100 |
| Perfume oil P1. P2. P3 or P4 | Fragrance | 0.5 |
| Euxyl ® K703 | Phenoxyethanol, Benzoic Acid, Dehydroacetic Acid | 0.2 |
| 4-Hydroxyacetophenone | Hydroxyacetophenone | 0.3 |
| Pentyl lactate | | 0.2 |
| Butyl lactate | | 0.2 |
| p-Hydroxy benzaldehyde | | 0.1 |

TABLE 8

Intimate wash (Amounts in % b.w.)

| Ingredients | INCI Name | Amount |
|---|---|---|
| Tegobetaine HS | Cocamidopropyl Betaine. Glyceryl Laurate | 15.0 |
| Tagat L 2 | PEG-20 Glyceryl Laurate | 2.0 |
| Arlacide G | Chlorhexidine Digluconate | 0.1 |
| Rewoquat B 50 | Benzalkonium Chloride | 0.1 |
| Lactic Acid. 80% | Lactic Acid | 0.1 |
| Water | Water | Ad 100 |
| Perfume oil P1. P2. P3 or P4 | Fragrance | 0.2 |
| Euxyl ® K700 | Potassium Sorbate, Benzyl Alcohol, Phenoxyethanol | 0.3 |
| Hydrolite ® 5 | Pentlyene Glycol | 2.0 |
| Isoamyl lactate | | 0.2 |
| Butyl lactate | | 0.4 |
| p-Anisic acid | | 0.1 |

TABLE 9

Shampoo (Amounts in % b.w.)

| Ingredients | Amount |
|---|---|
| Sodium lauryl ether sulfate (e.g. Texapon NSO) | 12 |
| Cocamidopropyl betaine (e.g. Dehyton K) | 2 |
| Sodium chloride | 1.4 |
| Citric acid | 1.3 |
| Perfume oil P1. P2. P3 or P4 | 0.3 |
| Phenoxyethanol, methyl-, ethyl-, butyl- and propylparaben | 0.2 |
| Butyl lactate | 0.3 |
| Benzl lactate | 0.1 |
| p-Hydroxy benzaldehyde | 0.05 |
| p-Anisic aldehyde | 0.05 |
| Water | Ad 100 |

TABLE 10

2-in-1 Shampoo (Amounts in % b.w.)

| Ingredients | INCI Name | Amount |
|---|---|---|
| Deionized water | Water | Ad 100 |
| Plantacare PS 10 | Sodium Laureth Sulfate. Lauryl Glucoside | 20.0 |
| Euperlan PK 771 | Glycol Distearate. Sodium Lauryl Sulfate. Cocamide MEA. Laureth-10 | 6.0 |
| Sodium chloride | Sodium Chloride | 1.4 |
| Citric acid monohydrate crystalline | Citric acid | 0.1 |
| Perfume oil P1. P2. P3 or P4 | Fragrance | 0.5 |
| 4-Hydroxyacetophenone | Hydroxyacetophenone | 0.4 |
| Butyl lactate | | 0.4 |
| 3-Phenylpropanol | | 0.1 |
| p-Hydroxy benzaldehyde | | 0.08 |

TABLE 11

Anti-dandruff Shampoo (Amounts in % b.w.)

| Ingredients | Amount |
|---|---|
| Climbazole | 0.50 |
| Sodium Laureth Sulfate | 37.00 |
| Cocamidopropyl Betaine | 8.00 |
| PEG-6 Caprylic/Capric Glycerides | 2.50 |
| Laureth-2 | 2.00 |
| Water (Aqua). Glycerol. *Thymus Vulgaris* (Thyme). Flower/Leaf Extract | 0.50 |
| *Rosmarinus Officinalis* (Rosemary) Leaf Water. Water (Aqua). Butylene Glycol. Pentylene Glycol | 0.50 |
| Bisabolol | 0.10 |
| Panthenol | 0.50 |
| Polyquaternium-10 | 0.40 |
| Perfume oil P1. P2. P3 or P4 | 0.50 |
| Phenoxyethanol, Methylparaben, Ethylparaben, Butylparaben, Propylparaben, Isobutylparaben | 0.50 |
| Pentyl lactate | 0.40 |
| Benzyl alcohol | 0.20 |
| Phenyl ethyl alcohol | 0.10 |
| Water (Aqua) | Ad 100 |

TABLE 12

Hair conditioner with Crinipan. rinse-off (Amounts in % b.w.)

| Ingredients | INCI Name | Amount |
|---|---|---|
| Lanette ® O | Cetearyl Alcohol | 4.00 |
| Dragoxat 89 | Ethylhexyl Isononanoate | 2.00 |
| Genamin ® KDM-P | Behentrimonium Chloride | 1.00 |
| SF 1550 | Phenyl Trimethicone | 0.10 |
| Neo Heliopan ® BB | Benzophenone-3 | 0.10 |
| Crinipan ® AD | Climbazole | 0.80 |
| Glycerol 99.5 P. | Glycerol | 6.00 |
| Water | Water (Aqua) | Ad 100 |
| Actipone ® Alpha Pulp | Water (Aqua). Butylene Glycol. Malic Acid. *Actinidia Chinensis* (Kiwi) Fruit Juice. Citrus. | 0.50 |

TABLE 12-continued

Hair conditioner with Crinipan. rinse-off (Amounts in % b.w.)

| Ingredients | INCI Name | Amount |
|---|---|---|
| | *Aurantium Dulcis* (Orange). Juice. *Citrus Paradisi* (Grapefruit) Juice. *Pyrus Malus* (Apple) Juice. Trideceth-9. *Prunus Amygdalus Dulcis* (Sweet Almond) Seed Extract | |
| Extrapone ® Bamboo P | Propylene Glycol. Water (Aqua). Butylene Glycol. *Bambusa Vulgaris* Shoot Extract | 0.50 |
| Sodium Hydroxide 10% solution | Sodium Hydroxide | 0.40 |
| Colour I | Colour | 0.60 |
| Colour II | Colour | 0.30 |
| Perfume oil P1. P2. P3 or P4 | Fragrance | 0.40 |
| Preservative | Methylparaben | 0.20 |
| Butyl lactate | | 0.50 |
| Phenylethyl alcohol | | 0.10 |
| p-Anisic aldehyde | | 0.10 |

TABLE 13

Shower gel (Amounts in % b.w.)

| Ingredients | INCI | Amount |
|---|---|---|
| Deionized water | Water | Ad 100 |
| Plantacare PS 10 | Sodium Laureth Sulfate. Lauryl Glucoside | 20.0 |
| Sodium chloride | Sodium Chloride | 1.4 |
| Citric acid monohydrate crystalline | Citric Acid | 1.3 |
| Perfume oil P1. P2. P3 or P4 | Fragrance | 0.6 |
| SymDiol ®68 | 1,2-hexanediol, caprylyl glycol | 0.4 |
| Pentyl lactate | | 0.4 |
| Isoamyl lactate | | 0.1 |
| p-Hydroxy benzaldehyde | | 0.1 |

TABLE 14

Shaving foam (Amounts in % b.w.)

| Ingredients | Amount |
|---|---|
| Dem. Water | Ad 100 |
| Triethanolamine | 4.0 |
| Edenor L2 SM (Stearinic acid. Palmitinic acid) (Cognis) | 5.3 |
| Laureth-23 | 3.0 |
| Stearylalcohol | 0.5 |
| Sodium lauryl sulfate | 3.0 |
| Extrapone Seaweed (water. propylene glycol. potassium iodide. *Fucus Vesiculosus* Extract) | 1.0 |
| Dragosantol (Bisabolol. Farnesol) | 0.1 |
| Perfume oil P1. P2. P3 or P4 | 1.0 |
| euxyl ® K220 (Methylisothiazolinone. Ethylhexylglyerol) | 0.4 |
| Butyl lactate | 0.4 |
| 3-Phenylpropanol | 0.05 |
| Propane, butane 4.2 Bar | 4.0 |

TABLE 15

Depilatory cream (Amounts in % b.w.)

| Ingredients | Amount |
|---|---|
| Cetearyl alcohol | 10.0 |
| Ceteareth-12 | 2.0 |
| PCL-Liquid (Cetearylethylhexanoate. Isopropylmyristate) | 3.0 |
| Dragosantol (Bisabolol. Farnesol) | 0.1 |
| Edenor L2 SM (Stearinic acid. Palmitinic acid) | 1.0 |
| Dem. Water | 52.2 |
| Urea | 5.0 |
| Dem. Water | Ad 100 |
| Calcium thioglycolate | 6.0 |
| Sodium hydroxide solution. 10% | 10.0 |
| Perfume oil P1. P2. P3 or P4 | 0.5 |
| Neo Dragocid Powder (Methyl parabene, sorbic acid, Dehydro acetic acid, Propyl parabene) | 0.4 |
| Butyl lactate | 0.4 |
| Propyl lactate | 0.2 |
| p-Anisic aldehyde | 0.15 |

TABLE 16

After Shave Tonic (Amounts in % b.w.)

| Ingredients | INCI | Amount |
|---|---|---|
| SymSol ® PF-3 | Water (Aqua). Pentylene Glycol. Sodium Lauryl Sulfoacetate. SodiumOleoyl Sarcosinate. Sodium Chloride. Disodium Sulfoacetate. Sodium Oleate | 3.00 |
| SymSitive ® 1609 | Pentylene Glycol. 4-t-Butylcyclohexanol | 1.00 |
| Frescolat ® ML | Menthyl Lactate | 0.30 |
| Glycerol 99.5 P. | Glycerol | 5.00 |
| Water | Water (Aqua) | Ad 100 |
| Extrapone ® Glacier Water GW | Glycerol. Water (Aqua) | 1.00 |
| SymCalmin ® | Butylene Glycol. Pentylene Glycol. Hydroxyphenyl Propamidobenzoic Acid | 0.50 |
| Dragosine ® | Carnosine | 0.10 |
| Hydrolite ® 5 | Pentylene Glycol | 5.00 |
| Ethanol 96% | Alcohol Denat. | 5.00 |

TABLE 16-continued

After Shave Tonic (Amounts in % b.w.)

| Ingredients | INCI | Amount |
|---|---|---|
| Colour Pigment | Colour Pigment | 0.05 |
| Perfume oil P1. P2. P3 or P4 | Parfum | 0.15 |
| Butyl lactate | | 0.60 |
| p-Anisic aldehyde | | 0.10 |

TABLE 17

Deodorant formulation in the form of a roll-on gel (Amounts in % b.w.)

| Ingredients | Amount |
|---|---|
| 1,3-butylene glycol | 2.00 |
| PEG-40-hydrogenated castor oil | 2.00 |
| Hydroxyethylcellulose | 0.50 |
| Perfume oil P1. P2. P3 or P4 | 0.30 |
| 1,3-propanediol | 0.50 |
| 3-Phenylpropanol | 0.30 |
| Ethylhexyl glycerin | 0.10 |
| Butyl lactate | 0.50 |
| Phenyl ethyl alcohol | 0.10 |
| p-Anisic acid | 0.30 |
| Water | ad 100.00 |

TABLE 18

Clear deo anti-perspirant roll-on (Amounts in % b.w.)

| Ingredients | INCI | Amount |
|---|---|---|
| Methocel E4M Premium | Hydroxypropyl Methylcellulose | 0.50 |
| Water | Water (Aqua) | Ad 100 |
| Neo-PCL Water Soluble N | Trideceth-9. PEG-5 Ethylhexanoate. Water (Aqua) | 1.00 |
| Solubilizer | PEG-40 Hydrogenated Castor Oil. Trideceth-9. Propylene Glycol. Water (Aqua) | 3.00 |
| Deolite | Dimethyl Phenylpropanol. Pentylene Glycol | 0.50 |
| Locron LW | Aluminium Chlorohydrate | 25.00 |
| Aloe Vera Gel Concentrate 10/1 | *Aloe Barbadensis* Leaf Juice | 1.00 |
| Propylene Glycol-1.2 99 P GC | Propylene Glycol | 4.00 |
| Ethanol 96% | Alcohol Denat. | 30.00 |
| Perfume oil P1. P2. P3 or P4 | Parfum | 1.00 |
| Butyl lactate | | 0.45 |
| p-Anisic acid | | 0.1 |

TABLE 19

Deodorant stick (Amounts in % b.w.)

| Ingredients | Amount |
|---|---|
| Sodium stearate | 8.00 |
| PPG-3 Myristyl ether | 70.00 |
| 1.2-propylene glycol | 10.00 |
| 1.1-dimethyl-3-phenylpropanol | 0.20 |
| 2-butyloctanoic acid | 0.20 |
| Perfume oil P1. P2. P3 or P4 | 0.60 |
| Heptoxy-1.2-propanediol | 0.20 |
| Phenoxyethanol | 0.30 |
| Butyl lactate | 0.40 |
| 3-Phenylpropanol | 0.20 |
| Water | Ad 100 |

TABLE 20

Zirconium suspensoid antiperspirant stick (Amounts in % b.w.)

| Ingredients | INCI | Amount |
|---|---|---|
| PCL Liquid 100 | Cetearyl ethylhexanonate | Ad 100 |
| Silicone Fluid 345 | Cyclomethicone | 10.00 |
| CRODACOL C90 | Cetyl Alcohol | 8.00 |
| SYNCROWAX HGLC | C18-36 Triglyceride | 8.00 |
| CRODAMOL PTC | Pentaerythritol Tetracaprylate/Caprate | 5.00 |
| SYNCROWAX HRC | Tribehenin | 4.00 |
| VOLPO N5 | Oleth-5 | 1.00 |
| Titanium Dioxide | | 1.00 |
| Rezal 36GP | Aluminium Tetrachlorohydrex GLY | 20.00 |
| Dry Flo C | Aluminium Starch Octenyl Succinate | 22.50 |
| Perfume oil P1. P2. P3 or P4 | Parfum | 0.60 |
| Preservative | Phenoxyethanol | 0.40 |
| Hexoxy-1,2-propanediol | | 0.10 |
| Pentyl lactate | | 0.40 |
| Propyl lactate | | 0.10 |
| p-Hydroxy benzaldehyde | | 0.10 |

TABLE 21

Deodorant pump spray with SymClariol (Amounts in % b.w.)

| Ingredients | INCI | Amount |
|---|---|---|
| SymClariol ® | Decylene Glycol | 0.50 |
| Solubilizer | PEG-40 Hydrogenated Castor Oil. Trideceth-9. Propylene Glycol. Water (Aqua) | 4.00 |
| Neo-PCL Water Soluble N | Trideceth-9. PEG-5 Ethylhexanoate. Aqua | 1.50 |
| SymRelief ® | Bisabolol. *Zingiber Officinale* (Ginger) Root Extract | 0.10 |
| Water | Water (Aqua) | Ad 100 |
| 1,2-Propylene Glycol | Propylene Glycol | 6.00 |
| Perfume oil P1. P2. P3 or P4 | Perfume | 0.40 |
| SymDiol ® 68 | 1,2-Hexanediol, Caprylyl Glycol | 0.30 |
| Butyl lactate | | 0.40 |
| p-Anisic aldehyde | | 0.10 |

TABLE 22

Antiperspirant formulations (Amounts in % b.w.)

| Ingredients | Amounts |
|---|---|
| Reach AZP-908 SUF | 24.00 |
| Cyclomethicone (Pentamer) | Ad 100 |
| Polydecene (Silkflo 364 NF) | 17.50 |
| Neo Heliopan OS (ethylhexyl salicylate) | 2.50 |
| L-Menthyl lactate (Frescolate ML) | 0.25 |
| Polyethylene | 3.00 |
| Hydrogenated castor oil | 2.00 |
| Promyristyl PM-3 | 7.00 |
| PEG-8 Distearate | 3.00 |
| Silicon dioxide (Cab-O-Sil M-5) | 1.00 |
| Stearyl alcohol | 15.00 |
| Octyldodecanol | 0.10 |

TABLE 22-continued

Antiperspirant formulations (Amounts in % b.w.)

| Ingredients | Amounts |
|---|---|
| Perfume oil P1. P2. P3 or P4 | 0.80 |
| 3-Phenylpropanol | 0.40 |
| Butyl lactate | 0.40 |
| p-Anisic aldehyde | 0.10 |

TABLE 23

O/W lotion (Amounts in % b.w.)

| Ingredients | Amount |
|---|---|
| Paraffin oil | 5.00 |
| Isopropyl palmitate | 5.00 |
| Cetyl alcohol | 2.00 |
| Beeswax | 2.00 |
| Ceteareth-20 | 2.00 |
| PEG-20-glyceryl stearate | 1.50 |
| Glycerol | 3.00 |
| Perfume oil P1. P2. P3 or P4 | 0.30 |
| Hydrolite ® 5 (Pentylene Glycol) | 1.00 |
| 4-Hydroxyacetophenone | 0.30 |
| Butyl lactate | 0.40 |
| Pentyl lactate | 0.10 |
| p-Hydroxy benzaldehyde | 0.10 |
| Water | ad 100.00 |

TABLE 24

Body lotion (Amounts in % b.w.)

| Ingredients | Amount |
|---|---|
| Cetearyl Alcohol | 2.00 |
| Ethylhexyl Isononanoate | 5.00 |
| Cetearyl Ethylhexanoate. Isopropyl Myristate | 3.00 |
| Glyceryl Oleate Citrate. Caprylic/Capric Triglyceride | 4.00 |
| Water (Aqua) | Ad 100 |
| Carbomer | 0.30 |
| Sodium Benzoate | 0.100 |
| Propylene Glycol | 5.00 |
| Sodium Hydroxide 30% solution | 0.30 |
| Perfume oil P1. P2. P3 or P4 | 0.30 |
| Hydrolite ® 5 (Pentylene Glycol) | 1.00 |
| Triethylene Glycol, Imidazolidinyl Urea, Methylparaben, Propylparaben, Dehydroacetic Acid | 0.30 |
| Benzyl lactate | 0.40 |
| p-Anisic aldehyde | 0.10 |

TABLE 25

Cream (Amounts in % b.w.)

| Ingredients | INCI | Amount |
|---|---|---|
| Dracorin ® CE | Glyceryl Stearate Citrate | 1.00 |
| Lanette ® O | Cetearyl Alcohol | 2.00 |
| Cutina ® GMS-V | Glyceryl Stearate | 1.00 |
| Tegosoft ® MM | Myristyl Myristate | 1.00 |
| Xiameter ® PMX-0246. Cyclosiloxane | Cyclohexasiloxane (and) Cyclopentasiloxane | 0.50 |
| Dragoxat ® 89 | Ethylhexyl Isononanoate | 2.00 |
| PCL-Liquid 100 | Cetearyl Ethylhexanoate | 4.00 |
| Neutral Oil | Caprylic/Capric Triglyceride | 4.00 |
| Carbopol ® Ultrez 21 | Acrylates/C10-30 Alkyl Acrylate Crosspolymer | 0.20 |
| Keltrol ® CG-T | Xanthan Gum | 0.10 |
| Water | Water (Aqua) | Ad 100 |
| Glycerol 99.5 P. | Glycerol | 3.00 |

TABLE 25-continued

Cream (Amounts in % b.w.)

| Ingredients | INCI | Amount |
|---|---|---|
| Propylene Glycol-1.2 99 P GC | Propylene Glycol | 2.00 |
| Sodium Benzoate | Sodium Benzoate | 0.10 |
| Sodium Hydroxide 10% solution | Sodium Hydroxide | 0.50 |
| Perfume oil P1. P2. P3 or P4 | Perfume | 0.30 |
| Euxyl ® K702 | Dehydroacetic Acid, Benzoic Acid, Phenoxyethanol, Polyaminopropyl Biguanide, Ethylhexylglycerin | 0.30 |
| Butyl lactate | | 0.40 |
| 3-Phenylpropanol | | 0.10 |

TABLE 26

Hand and body cream (Amounts in % b.w.)

| Ingredients | INCI | Amount |
|---|---|---|
| Dracorin ® GOC | Glyceryl Oleate Citrate. Caprylic/Capric Triglyceride | 2.00 |
| PCL-Solid | Stearyl Heptanoate. Stearyl Caprylate | 2.50 |
| Lanette ® O | Cetearyl Alcohol | 1.50 |
| Cutina ® GMS-V | Glyceryl Stearate | 1.00 |
| Dragoxat ® 89 | Ethylhexyl Isononanoate | 3.00 |
| PCL-Liquid 100 | Cetearyl Ethylhexanoate | 7.00 |
| Isodragol ® | Triisononanoin | 4.00 |
| Xiameter ® PMX-0345 Cyclosiloxane | Cyclopentasiloxane (and) Cyclohexasiloxane | 0.50 |
| Water | Water (Aqua) | Ad 100 |
| Carbopol ® Ultrez 21 | Acrylates/C10-30 Alkyl Acrylate Crosspolymer | 0.20 |
| Keltrol ® CG-RD | Xanthan Gum | 0.10 |
| Glycerol 85 P. | Glycerol | 3.00 |
| DragoBetaGlucan | Water (Aqua). Butylene Glycol. Glycerol. *Avena Sativa* (Oat) Kernel Extract | 1.50 |
| Potassium Sorbat | Potassium Sorbate | 0.10 |
| Sodium Hydroxide 10% solution | Sodium Hydroxide | 0.50 |
| Perfume oil P1. P2. P3 or P4 | Parfum | 0.20 |
| SymDiol ®68 | 1,2-hexanediol, caprylyl glycol | 0.30 |
| Butyl lactate | Hydroxyacetophenone | 0.30 |
| Propyl lactate | | 0.30 |
| p-Anisic aldehyde | | 0.06 |

TABLE 27

Face cream (Amounts in % b.w.)

| Ingredients | INCI | Amount |
|---|---|---|
| Emulsiphos ® | Potassium Cetyl Phosphate. Hydrogenated Palm Glycerides | 1.50 |
| Cutina ® GMS-V | Glyceryl Stearate | 1.70 |
| Lanette ® O | Cetearyl Alcohol | 3.00 |
| Tegosoft ® MM | Myristyl Myristate | 1.00 |
| PCL-Liquid 100 | Cetearyl Ethylhexanoate | 1.00 |
| Isodragol ® | Triisononanoin | 3.00 |
| Dragoxat ® 89 | Ethylhexyl Isononanoate | 4.00 |
| Avocado Oil | *Persea Gratissima* (Avocado) Oil | 3.00 |
| Abil ® 350 | Dimethicone | 0.50 |
| Coyi-ox ® T-70 | Tocopherol | 0.10 |
| Edeta ® BD | Disodium EDTA | 0.10 |
| Carbopol ® Ultrez 21 | Acrylates/C10-30 Alkyl Acrylate Crosspolymer | 0.30 |
| Keltrol ® CG-RD | Xanthan Gum | 0.150 |
| Water | Water (Aqua) | Ad 100 |

TABLE 27-continued

Face cream (Amounts in % b.w.)

| Ingredients | INCI | Amount |
| --- | --- | --- |
| Glycerol 99.5 P. | Glycerol | 4.00 |
| Hydrolite ® 5 | Pentylene Glycol | 0.50 |
| Propylene Glycol-1.2 99 P GC | Propylene Glycol | 3.00 |
| SymMatrix ® | Maltodextrin. *Rubus Fruticosus* (Blackberry) Leaf Extract | 0.50 |
| Sodium Hydroxide 10% solution | Sodium Hydroxide | 0.50 |
| Perfume oil P1. P2. P3 or P4 | Parfum | 0.30 |
| Euxyl ® K712 | Sodium Benzoate. Potassium Sorbate | 0.20 |
| Butyl lactate | | 0.40 |
| 3-Phenylpropanol | | 0.20 |
| Phenyl ethyl alcohol | | 0.10 |

TABLE 28

Moisturizing body care cream (Amounts in % b.w.)

| Ingredient | Amount |
| --- | --- |
| PEG-7 hydrogenated castor oil | 6.00 |
| Cetearyl ethyl hexanoate | 10.00 |
| Isopropyl myristate | 5.00 |
| Mineral oil | 7.00 |
| Shea Butter (*Butyrospermum parkii*) | 0.50 |
| Aluminum stearate | 0.50 |
| Magnesium stearate | 0.50 |
| Bisabolol | 0.20 |
| Quaternium-18-Hectorit | 0.70 |
| Dipropylene glycol | 5.0 |
| Magnesium sulfate | 0.70 |
| Pentylene glycol | 4.00 |
| Perfume oil P1. P2. P3 or P4 | 0.30 |
| 4-Hydroxyacetophenone | 0.40 |
| Butyl lactate | 0.30 |
| p-Anisic acid | 0.10 |
| Aqua dem. | Ad 100 |

TABLE 29

Anti-wrinkle cream (Amounts in % b.w.)

| Ingredients | Amount |
| --- | --- |
| Glyceryl Stearate Citrate | 1.00 |
| Glyceryl Laurate | 1.00 |
| Cetearyl Alcohol (and) Myristyl Myristate | 3.00 |
| Cetearyl Ethylhexanoate | 4.00 |
| Mineral oil | 4.00 |
| Cyclopentasiloxane, Cyclohexasiloxane | 0.50 |
| Acrylates/C10-30 Alkyl Acrylate Crosspolymer | 0.20 |
| Water | Ad 100 |
| 1,2-Hexanediol | 2.00 |
| Sodium Hydroxide 10% solution | 0.10 |
| *Narcissus Tazetta* Bulb Extract | 1.00 |
| Perfume oil P1. P2. P3 or P4 | 0.30 |
| Preservative (Phenoxyethanol) | 0.50 |
| Butyl lactate | 0.40 |
| Isoamyl lactate | 0.10 |
| p-Hydroxy benzaldehyde | 0.10 |

TABLE 30

Anti-septic wound cream (Amounts in % b.w.)

| Ingredients (INCI) | Amount |
| --- | --- |
| Sorbitan Isostearate. Hydrogenated Castor Oil. Ceresin. Beeswax (Cera Alba) | 6.00 |
| Petrolatum | 21.00 |
| Cera Alba | 5.00 |
| Cetearyl Alcohol | 7.00 |
| *Prunus Dulcis* | 7.00 |
| Lanolin | 5.00 |
| Paraffinum Liquidum | 12.00 |
| Perfume oil P1. P2. P3 or P4 | 0.30 |
| Water (Aqua) | Ad 100 |
| Panthenol | 7.00 |
| Magnesium Sulfate | 0.70 |
| Pentylene Glycol | 1.00 |
| Tocopheryl Acetate | 1.00 |
| Octenidine dihydrochloride | 0.10 |
| Phenoxyethanol | 0.50 |
| Butyl lactate | 0.40 |
| p-Anisic aldehyde | 0.10 |

TABLE 31

Anti-acne wash (Amounts in % b.w.)

| Ingredients (INCI) | Amount |
| --- | --- |
| Water (Aqua) | Ad 100 |
| Polyquaternium-7 | 0.50 |
| Cocamidopropyl Betaine 9.000 | 9.00 |
| Coco Glucoside 2.000 | 2.00 |
| Polysorbate 80. Glycerol. *Gossypium Herbaceum*. (Cotton) Seed Oil. Water (Aqua) | 1.00 |
| Trideceth-9. PEG-5 Ethylhexanoate. Water (Aqua) | 1.00 |
| Glycereth-90 Isostearate. Laureth-2 | 0.50 |
| Sodium Laureth Sulfate 37.000 | 37.00 |
| Glycerol. *Triticum Vulgare* (Wheat) Gluten. Water (Aqua) | 1.00 |
| Sodium Chloride | 0.30 |
| Perfume oil P1. P2. P3 or P4 | 1.00 |
| 1,2-hexanediol, caprylyl glycol | 0.40 |
| 4-Hydroxyacetophenone | 0.30 |
| Butyl lactate | 0.20 |
| Propyl lactate | |
| p-Anisic aldehyde | 0.08 |

TABLE 32

Cosmetic sun protection composition (Amounts in % b.w.)

| Ingredient | Amount |
| --- | --- |
| Ethylhexyl cinnamic acid | 7.50 |
| Benzophenon-3 | 2.00 |
| Polyglyceryl dimer soyate | 0.80 |
| Sorbitane stearate | 1.00 |
| Tocopheryl acetate | 0.50 |
| Glyceryl stearate. PEG-100 Stearate | 3.00 |
| PEG-40. hydrogenated castor oil | 1.00 |
| Titanium dioxide. aluminum oxide hydrate. Dimethicon/Methicon Copolymer | 3.00 |
| *Butyrospermum parkii* (Shea Butter) | 1.00 |
| $C_{12-15}$ alkyl benzoate | 6.50 |
| Butylene glycol | 5.00 |
| Xanthan gum | 0.30 |
| Allantoin | 0.10 |
| Polyacryl amide. $C_{13-14}$ isoparaffin. Laureth-7 | 1.00 |
| Pentylene glycol | 5.00 |
| 4-t Butylcyclohexanol | 1.00 |
| Perfume oil P1. P2. P3 or P4 | 0.30 |
| Preservatives (Methyl-. Butyl-. Ethyl-. Propylparaben. Phenoxyethanol) | 0.30 |
| Butyl lactate | 0.30 |
| Pentyl lactate | 0.30 |

TABLE 32-continued

Cosmetic sun protection composition (Amounts in % b.w.)

| Ingredient | Amount |
|---|---|
| p-Anisic aldehyde | 0.10 |
| Aqua dem. | Ad 100 |

TABLE 33

Sun protection spray (Amounts in % b.w.)

| Ingredients | INCI | Amount |
|---|---|---|
| Water. demineralized | Water (aqua) | Ad 100 |
| Glycerol | Glycerol | 4.00 |
| 1.3 butylene glycol | Butylene glycol | 5.00 |
| D-Panthenol | Panthenol | 0.50 |
| Lara Care A-200 | Galactoarabinan | 0.25 |
| Baysilone oil M 10 | Dimethicone | 1.00 |
| Edeta BD | Disodium EDTA | 0.10 |
| Copherol 1250 | Tocopheryl acetate | 0.50 |
| Cetiol OE | Dicaprylyl ether | 3.00 |
| Neo Heliopan ® HMS | Homosalate | 5.00 |
| Neo Heliopan ® AV | Ethylhexyl methoxycinnamate | 6.00 |
| Neo Heliopan ® 357 | Butyl methoxydibenzoylmethane | 1.00 |
| Corapan TQ | Diethylhexylnaphthalate | 2.00 |
| Alpha Bisabolol | Bisabolol | 0.10 |
| Pemulen TR-2 | Acrylates/C10-30 alkyl acrylate crosspolymer | 0.25 |
| NaOH. 10% | Sodium hydroxide | 0.60 |
| Perfume oil P1. P2. P3 or P4 | Fragrance | 0.20 |
| Phenoxyethanol | Phenoxyethanol | 0.40 |
| Solbrol M | Methylparaben | 0.10 |
| Solbrol P | Propylparaben | 0.10 |
| Butyl lactate | | 0.50 |
| Benzyl lactate | | 0.20 |
| p-Anisic aldehyde | | 0.10 |

TABLE 34

Sunscreen spray O/W. SPE 15-20 (Amounts in % b.w.)

| Ingredients | INCI | Amount |
|---|---|---|
| Dracorin ® GOC | Glyceryl Oleate Citrate. Caprylic/Capric Triglyceride | 2.00 |
| Corapan ® TQ | Diethylhexyl 2.6-Naphtalate | 3.00 |
| Neo Heliopan ® HMS | Homosalate | 7.00 |
| Neo Heliopan ® OS | Ethylhexyl Salicylate | 5.00 |
| Neo Heliopan ® 357 | Butyl Methoxydibenzoylmethane | 3.00 |
| Isoadipate | Diisopropyl Adipate | 6.00 |
| Baysilone ® Oil M10 | Dimethicone | 1.00 |
| Edeta ® BD | Disodium EDTA | 0.10 |
| Vitamin E Acetate | Tocopheryl Acetate | 0.50 |
| Dragosantol ® 100 | Bisabolol | 0.10 |
| Pemulen ® TR-2 | Acrylates/C10-30 Alkyl Acrylate Crosspolymer | 0.25 |
| Water | Water (Aqua) | Ad 100 |
| Glycerol 99.5 P. | Glycerol | 4.00 |
| Butylene Glycol | Butylene Glycol | 5.00 |
| Neo Heliopan ® Hydro (103089). used as 25% aq. solution neutralized with Biotive ® L-Arginine | Phenylbenzimidazole Sulfonic Acid | 8.00 |
| Biotive ® L-Arginine | Arginine | 0.55 |
| Perfume oil P1. P2. P3 or P4 | Fragrance | 0.40 |
| 4-Hydroxyacetophenone | Hydroxyacetophenone | 0.40 |
| SymDiol ® 68 | 1,2-Hexanediol, Caprylyl glycol | 0.30 |
| Pentyl lactate | | 0.25 |
| Butyl lactate | | 0.40 |
| 3-Phenylpropanol | | 0.10 |

TABLE 35

Sun protection soft cream (W/O). SPF 40 (Amounts in % b.w.)

| Ingredients | INCI | Amount |
|---|---|---|
| Dehymuls PGPH | Polyglyceryl-2 dipolyhydroxystearate | 5.00 |
| Copherol 1250 | Tocopheryl acetate | 0.50 |
| Permulgin 3220 | Ozocerite | 0.50 |
| Zinc stearate | Zinc stearate | 0.50 |
| Tegosoft TN | C12-15 Alkyl benzoate | 10.00 |
| Neo Heliopan ® E1000 | Isoamyl-p-methoxycinnamate | 2.00 |
| Neo Heliopan ® 303 | Octocrylene | 5.00 |
| Neo Heliopan ® MBC | 4-Methylbenzylidene camphor | 3.00 |
| Zinc oxide. neutral | Zinc oxide | 5.00 |
| Water. distilled | Water (aqua) | Add 100 |
| EDETA BD | Disodium EDTA | 0.10 |
| Glycerol | Glycerol | 4.00 |
| Magnesium sulfate | Magnesium sulfate | 0.50 |
| Perfume oil P1. P2. P3 or P4 | Parfum | 0.30 |
| Symdiol ® 68 | 1,2-Hexanediol, Caprylylglycol | 0.50 |
| 4-Hydroxyacetophenone | Hydroxyacetophenone | 0.30 |
| Butyl lactate | | 0.20 |
| p-Anisic aldehyde | | 0.10 |

TABLE 36

Sun protection milk (W/O) (Amounts in % b.w.)

| Ingredients | INCI | Amount |
|---|---|---|
| Dehymuls PGPH | Polyglyceryl-2 dipolyhydroxystearate | 3.00 |
| Beeswax 8100 | Beeswax | 1.00 |
| Monomuls 90-0-18 | Glyceryl oleate | 1.00 |
| Zinc stearate | Zinc stearate | 1.00 |
| Cetiol SN | Cetearyl isononanoate | 5.00 |
| Cetiol OE | Dicaprylyl ether | 5.00 |
| Tegosoft TN | C12-15 alkyl benzoate | 4.00 |
| Vitamin E | Tocopherol | 0.50 |
| Neo Heliopan ® OS | Ethylhexyl salicylate | 5.00 |
| Neo Heliopan ® AV | Ethylhexyl methoxycinnamate | 7.50 |
| Uvinul ® T150 | Ethylhexyl triazone | 1.50 |
| Water. distilled | Water (Aqua) | Ad 100 |
| Trilon BD | Disodium EDTA | 0.10 |
| Glycerol | Glycerol | 5.00 |
| Neo Heliopan ® AP 10% solution. neutralized with NaOH | Disodium phenyl dibenzimidazole tetrasulfonate | 15.00 |
| Perfume oil P1. P2. P3 or P4 | Parfum | 0.25 |
| Hydrolite ® 5 | Pentylene Glycol | 1.50 |
| Alpha bisabolol | Bisabolol | 0.10 |
| SymOcide ® PT | Phenoxyethanol. Tropolone | 0.20 |
| Butyl lactate | Hydroxyacetophenone | 0.20 |
| Isopantyl lactate | | 0.20 |
| p-Anisic acid | | 0.10 |
| p-Anisic aldehyde | | 0.10 |

TABLE 37

After sun gel (Amounts in % b.w.)

| Ingredients | INCI | Amount |
|---|---|---|
| SymSol ® PF-3 | Water (Aqua). Pentylene Glycol. Sodium Lauryl Sulfoacetate. SodiumOleoyl Sarcosinate. Sodium Chloride. Disodium Sulfoacetate. SodiumOleate. Sodium Sulfate | 3.000 |
| Glycerol 99.5 P. | Glycerol | 5.000 |
| SymHelios ® 1031 | Benzylidene Dimethoxydimethylin danone | 0.100 |
| Water | Water (Aqua) | Ad 100 |
| Pemulen ® TR-2 | Acrylates/C10-30 Alkyl Acrylate Crosspolymer | 1.000 |

TABLE 37-continued

After sun gel (Amounts in % b.w.)

| Ingredients | INCI | Amount |
|---|---|---|
| D-Panthenol 75 W | Panthenol | 0.500 |
| SymFinity ® 1298 | *Echinacea Purpurea* Extract | 0.100 |
| Extrapone ® Pearl GW | Water (Aqua). Glycerol. Hydrolyzed Pearl. Xanthan Gum | 1.000 |
| Sodium Hydroxide 10% solution | Sodium Hydroxide | 2.500 |
| Ethanol 96% | Alcohol Denat. | 15.000 |
| Perfume oil P1. P2. P3 or P4 | Parfum | 0.20 |
| SymOcide ® PS | Phenoxyethanol, 1,2-Hexanediol, Decyleneglycol | 0.50 |
| Butyl lactate | Hydroxyacetophenone | 0.40 |
| Phenylethyl alcohol | | 0.10 |
| p-Hydroxy benzaldehyde | | 0.10 |

TABLE 38

After sun lotion (Amounts in % b.w.)

| Ingredients | Amount |
|---|---|
| Acrylate/C10-30 alkylacrylate crosspolymer | 0.4 |
| Cetearylethyl hexanoate | 15.0 |
| Bisabolol | 0.2 |
| Tocopheryl acetate | 1.0 |
| Panthenol | 1.0 |
| Alcohol | 15.0 |
| Glycerol | 3.0 |
| Perfume oil P1. P2. P3 or P4 | 0.30 |
| 1,2-Hexanediol | 0.60 |
| Butyl lactate | 0.30 |
| p-Anisic aldehyde | 0.15 |
| Pentylene glycol | 4.0 |
| Aqua dem. | Ad 100 |
| Triethanolamine | 0.2 |

TABLE 39

Solution for wet wipes (Amounts in % b.w.)

| Ingredients | INCI | Amount |
|---|---|---|
| SymSol ® PF-3 | Water (Aqua). Pentylene Glycol. Sodium Lauryl Sulfoacetate. SodiumOleoyl Sarcosinate. Sodium Chloride. Disodium Sulfoacetate. SodiumOleate. Sodium Sulfate | 2.00 |
| Dragosantol ® 100 | Bisabolol | 0.10 |
| Glycerol 99.5 P. | Glycerol | 5.00 |
| Water | Water (Aqua) | Ad 100 |
| Hydrolite ® 5 | Pentylene Glycol | 5.00 |
| D-Panthenol 75 W | Panthenol | 0.80 |
| DragoCalm ® | Water (Aqua). Glycerol. *Avena Sativa* (Oat) Kernel Extract | 1.00 |
| Witch Hazel-Distillate | *Hamamelis Virginiana* (Witch Hazel) Water. Water (Aqua). Alcohol | 1.00 |
| Allplant Essence ® Org. Rose P | *Pelargonium Graveolens* Flower/Water | 1.00 |
| Perfume oil P1. P2. P3 or P4 | Parfum | 0.10 |
| Preservative | Phenoxyethanol | 0.30 |
| 4-Hydroxy-acetophenone | Hydroxyacetophenone | 0.30 |
| Butyl lactate | | 0.25 |
| Pentyl lactate | | 0.15 |
| p-Anisic aldehyde | | 0.05 |

TABLE 40

Peppermint Flavour PF1 (Amounts in ‰ b.w.)

| Ingredients | Amount |
|---|---|
| Substance of formula (I) | Add 1000 |
| Isobutyraldehyde | 0.5 |
| 3-Octanol | 0.5 |
| Dimethyl sulphide | 0.5 |
| trans-2-Hexenal | 1.0 |
| cis-3-Hexenol | 1.0 |
| 4-Terpineol. natural | 1.0 |
| Isopulegol | 1.0 |
| Piperitone. natural. from eucalyptus | 2.0 |
| Linalool | 3.0 |
| 8-Ocimenyl acetate. 10% in triacetin | 5.0 |
| Isoamyl alcohol | 10.0 |
| Isovaleraldehyde | 10.0 |
| alpha-Pinene. natural | 25.0 |
| beta-Pinene. natural | 25.0 |
| Neomenthol. racemic | 40.0 |
| Eucalyptol (1.8-cineol). natural | 50.0 |
| L-Menthyl acetate of the formula D | 70.0 |
| L-Menthone | 220.0 |
| D-Isomenthone | 50.0 |
| L-Menthol | 483.5 |
| Nonenolide | 1.0 |

TABLE 41

Wintergreen flavor PF2 (Amounts in % b.w.)

| Ingredients | Amount |
|---|---|
| Substance of formula (1) | 8 |
| Anethole | 9 |
| l-menthol (natural or synthetic) | 45 |
| Peppermint oil piperita type | 2 |
| Peppermint oil arvensis type | 3 |
| Spearmint oil spicata type | 1 |
| Eugenol | 7 |
| Eucalyptol | 5 |
| Methyl salicylate | 20 |

TABLE 42

Isoamylacetate type flavor PF3 (Amounts in % b.w.)

| Ingredients | Amount I | Amount II |
|---|---|---|
| Substance of formula (I) | 4 | 5 |
| Isoamylacetate | 2 | 2 |
| Ethylbutyrate | 0.5 | — |
| Butylbutyrate | — | 0.5 |
| Ethyl vanillin | 2 | — |
| Vanillin | — | 1 |
| Frambinon TM [4-(4-hydroxyphenyl)-2-butanon] | 0.5 | 0.5 |
| l-menthol | 8 | 11 |
| Triacetin | | 80 |
| 1.2-propylene glycol | 83 | |

TABLE 43

Cinnamon type cool flavor PF4 (Amounts in % b.w.)

| Ingredients | Amount |
|---|---|
| Substance of formula (I) | 3 |
| Menthlymethylether | 3 |
| Cinnamaldehyde | 10 |
| Anethole | 9 |
| Eugenol | 2 |
| l-menthol | 40 |
| Peppermint oil piperita type | 10 |

TABLE 43-continued

Cinnamon type cool flavor PF4 (Amounts in % b.w.)

| Ingredients | Amount |
| --- | --- |
| Peppermint oil arvensis type | 10 |
| Spearmint oil spicata type | 8 |
| (1R.2S.5R)-N-ethyl-2-isopropyl-5-methylcyclohexane-carboxamide (WS-3) | 2 |
| (1R.2S.5R)-N-[4-cyanomethylphenyl]-2-isopropyl-5-methylcyclohexane-carboxamide | 0.5 |
| Menthone glycerol ketal (Frescolat MGA ®) | 1.5 |
| Menthol propylene glycol carbonate (Frescolat MPC ®) | 1.5 |

TABLE 44

Toothpaste (Amounts in % b.w.)

| Ingredients | Amount |
| --- | --- |
| Water (deionized) | Ad 100 |
| Sorbitol 70% | 45.00 |
| Trisodiumphosphate | 0.10 |
| Saccharin | 0.20 |
| Sodiummonofluorophosphate | 1.14 |
| PEG 1500 | 5.00 |
| Sident 9 (abrasive silica) | 10.00 |
| Sident 22 S (Thickening silica) | 8.00 |
| Sodiumcarboxymethylcellulose | 1.10 |
| Titanium (IV) oxide | 0.50 |
| Water (deionized) | 4.50 |
| Sodiumlaurylsulfate (SLS) | 1.50 |
| Flavour (PF1. PF2. PF3 or PF4) | 1.00 |
| Solbrol M (Sodium salt) (Methylparaben) | 0.15 |
| Butyl lactate | 0.40 |
| Benzyl lactate | 0.10 |
| p-Anisic aldehyde | 0.10 |

TABLE 45

Toothpaste with zinc citrate (Amounts in % b.w.)

| Ingredients | Amount |
| --- | --- |
| Water (deionized) | Ad 100 |
| Sorbitol 70% | 45.00 |
| Trisodiumphosphate | 0.10 |
| Saccharin | 0.20 |
| Sodiummonofluorophosphate | 1.14 |
| PEG 1500 | 5.00 |
| Sident 9 (abrasive silica) | 10.00 |
| Sident 22 S (Thickening silica) | 8.00 |
| Sodiumcarboxymethylcellulose | 1.10 |
| Zinc citrate | 1.00 |
| Titanium (IV) oxide | 0.50 |
| Water (deionized) | 4.50 |
| Sodiumlaurylsulfate (SLS) | 1.50 |
| Flavour (PF1. PF2. PF3 or PF4) | 1.00 |
| SymDiol ® 68 (1.2-Hexanediol. Caprylylglycol) | 0.25 |
| Butyl lactate | 0.40 |
| Benzyl alcohol | 0.20 |

TABLE 46

Mouth rinse (Amounts in % b.w.)

| Ingredients | Amount |
| --- | --- |
| Ethylalcohol | 10.00 |
| Cremophor CO 40 (PEG 40 hydrogenated castor oil) | 1.00 |
| Flavour (PF1. PF2. PF3 or PF4) | 0.25 |
| Water (deionized) | Ad 100 |
| Sorbitol 70% | 5.00 |
| Sodiumsaccharin 450 | 0.07 |

TABLE 46-continued

Mouth rinse (Amounts in % b.w.)

| Ingredients | Amount |
| --- | --- |
| Sodiumfluoride | 0.18 |
| Benzoic acid | 0.12 |
| Butyl lactate | 0.40 |
| p-Anisic acid | 0.10 |

TABLE 47

Gel dental cream (Amounts in % b.w.)

| Ingredients | Amount |
| --- | --- |
| Na carboxymethylcellulose | 0.40 |
| Sorbitol 70%. in water | 72.00 |
| Polyethylene glycol (PEG) 1500 | 3.00 |
| Na saccarinate | 0.07 |
| Na fluoride | 0.24 |
| Flavor (PF1. PF2. PF3 or PF4) | 1.00 |
| Abrasive silica | 11.00 |
| Thickening silica | 6.00 |
| Sodium dodecyl sulfate (SDS) | 1.40 |
| Dist. water | Ad 100 |
| p-Hydroxybenzoic acid (PHB) ethyl ester | 0.15 |
| Butyl lactate | 0.40 |
| Propyl lactate | 0.20 |
| p-Anisic aldehyde | 0.20 |

TABLE 48

Dental cream against plaque (Amounts in % b.w.)

| Ingredients | Amount |
| --- | --- |
| Carrageenan | 0.90 |
| Glycerol | 15.00 |
| Sorbitol 70%. in water | 25.00 |
| PEG 1000 | 3.00 |
| Na fluoride | 0.24 |
| Tetrapotassium diphosphate | 4.50 |
| Tetrasodium diphosphate | 1.50 |
| Na saccarinate | 0.40 |
| Precipitated silica | 20.00 |
| Titanium dioxide | 1.00 |
| Triclosan | 0.30 |
| Spearmint flavor (comprising 60 wt. % l-carvone and 25 wt. % l-menthol) | 1.00 |
| Sodium dodecyl sulfate | 1.30 |
| Dist. water | Ad 100 |
| Benzylalcohol | 0.20 |
| Butyl lactate | 0.30 |
| Cis Hexenyl lactate | 0.10 |
| 3-Phenylpropanol | 0.05 |
| p-Anisic aldehyde | 0.10 |

TABLE 49

Dental cream for sensitive teeth (Amounts in % b.w.)

| Ingredients | Amount |
| --- | --- |
| Na carboxymethylcellulose | 0.70 |
| Xanthan gum | 0.50 |
| Glycerol | 15.00 |
| Sorbitol 70%. in water | 12.00 |
| Potassium nitrate | 5.00 |
| Sodium monofluorophosphate | 0.80 |
| Na saccharinate | 0.20 |
| Flavor (PF1. PF2. PF3 or PF4) | 1.00 |
| Ca-carbonate | 35.00 |
| Silicon dioxide | 1.00 |

TABLE 49-continued

Dental cream for sensitive teeth (Amounts in % b.w.)

| Ingredients | Amount |
| --- | --- |
| Sodium dodecyl sulfate (SDS) | 1.50 |
| Dist. water | Ad 100 |
| 4-Hydroxyacetophenone | 0.20 |
| Butyl lactate | 0.50 |
| p-Hydroxy benzaldehyde | 0.10 |

TABLE 50

Tooth cream and mouthwash 2-in-1 product (Amounts in % b.w.)

| Ingredients | Amount |
| --- | --- |
| Sorbitol | 40.00 |
| Glycerol | 20.00 |
| Ethanol | 5.00 |
| Water | Ad 100 |
| Na monofluorophosphate | 0.75 |
| Saccharin | 0.20 |
| Sident 9 (abrasive silicon dioxide) | 20.00 |
| Sident 22 S (thickening silicon dioxide) | 2.00 |
| Sodium carboxymethylcellulose | 0.30 |
| Sodium lauryl sulfate (SDS) | 1.20 |
| Color (Suspension. 1% in water) C.I. Pigment Blue 15 | 0.50 |
| Flavor (PF1. PF2. PF3 or PF4) | 0.90 |
| Solbrol M, sodium salt (methylparaben, sodium salt) | 0.20 |
| Butyl lactate | 0.30 |
| Pentyl lactate | 0.10 |
| p-Anisic aldehyde | 0.10 |

TABLE 51

Ready-to-use mouthwash with fluoride (Amounts in % b.w.)

| Ingredients | Amount |
| --- | --- |
| Ethanol | 7.00 |
| Glycerol | 12.00 |
| Na fluoride | 0.05 |
| Pluronic F-127 ® (BASF. surface-active substance) | 1.40 |
| Na phosphate buffer pH 7.0 | 1.10 |
| Na saccharinate | 0.10 |
| Flavour (PF1. PF2. PF3 or PF4) | 0.15 |
| Chlorhexidine digluconate | 0.2 |
| Dist. water | Ad 100 |
| Sorbic acid | 0.20 |
| Butyl lactate | 0.40 |
| p-Anisic aldehyde | 0.10 |

What claimed is:

1. A composition, consisting of (a) at least one lactate ester selected from the group consisting of

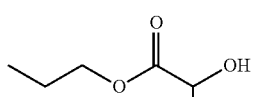

propyl lactate (Ia)

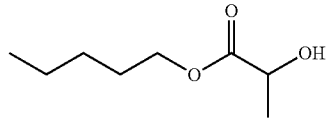

pentyl lactate (Ic)

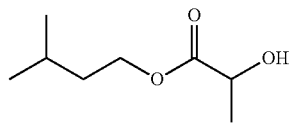

isopentyl lactate (Id)

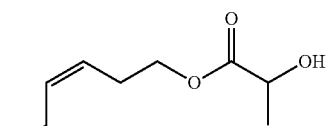

cis hexenyl lactate (Ie)

and,

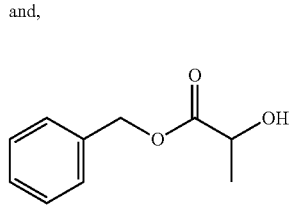

benzyl lactate (If)

a cosmetically acceptable salt thereof, a pharmaceutically acceptable salt thereof and mixtures thereof; and a component (b) selected from the group consisting of (b1) p-anisic aldehyde, (b2) 3-phenyl propanol, (b3) p-anisic acid and mixtures thereof; wherein compounds of formula (Ia), (Ic), (Id), (Ie) and (If) are used at 0.05 to 1% by weight (b.w.) and combined with components of (b) at 0.05 to 0.5% b.w.; and wherein the composition has antimicrobial activity.

2. The composition of claim 1, comprising at least one species selected from group (Ia), (Ic), (Id), (Ie) and (If) and wherein component (b) is selected from group consisting of a combination of (b1 and b2), (b2 and b3) and (b1 and b3).

3. A cosmetic or personal care composition, comprising the composition of claim 1.

4. The composition of claim 3, comprising the sum of compounds (a+b1+b2+b3) in an amount of 0.05 to 2% b.w.—calculated on the total composition.

5. The composition of claim 3, which is a skin care composition, a hair composition, a sun care composition or a fragrance composition.

6. A method for improving antimicrobial performance of a cosmetic or personal care composition comprising incorporating a working amount of the composition of claim 1.

7. The method of claim 6, wherein an amount of 0.05 to 2% b.w. of the sum of compounds (a+b1+b2+b3) is added to a cosmetic or personal care composition.

8. A composition comprising a mixture of compounds selected from the group consisting of
(1) butyl lactate at 1% and 3-phenylpropanol at 0.25%,
(2) butyl lactate at 1% and p-anisic acid at 0.25%,
(3) amyl lactate at 0.75% and p-anisic aldehyde at 0.25%,
(4) amyl lactate at 0.75% and 3-phenylpropanol at 0.25%,
(5) amyl lactate at 0.75% and p-anisic acid at 0.25%,
(6) benzyl lactate at 0.75% and p-anisic aldehyde at 0.25%,
(7) benzyl lactate at 0.75% and 3-phenylpropanol at 0.25%, and
(8) benzyl lactate at 0.75% and p-anisic acid at 0.25%; and
wherein the composition has antimicrobial activity.

9. A composition comprising a mixture of compounds, wherein the mixture of compounds is selected from the group consisting of
(1) butyl lactate at 1% and 3-phenylpropanol at 0.25%,
(2) amyl lactate at 0.75% and p-anisic aldehyde at 0.25%,
(3) amyl lactate at 0.75% and 3-phenylpropanol at 0.25%,
(4) benzyl lactate at 0.75% and p-anisic aldehyde at 0.25%, and
(5) benzyl lactate at 0.75% and 3-phenylpropanol at 0.25%.

10. A cosmetic or personal care composition comprising the composition of claim 8.

11. A cosmetic or personal care composition comprising the composition of claim 9.

12. The composition of claim 1, wherein the lactate ester (a) is selected from the group consisting of

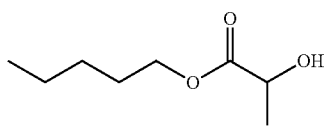

pentyl lactate (Ic)

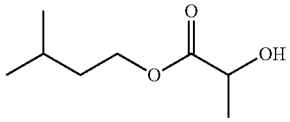

isopentyl lactate (Id)

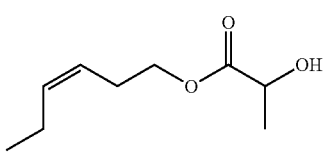

cis hexenyl lactate (Ie)

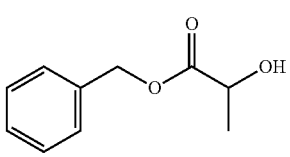

benzyl lactate (If)

a cosmetically acceptable salt thereof, a pharmaceutically acceptable salt thereof and mixtures thereof.

13. The composition of claim 1, wherein the composition is in the absence of 3-phenyl propanol.

14. The composition of claim 8, wherein:
mixture (1) is synergistic against gram negative bacterium *E. coli*;
mixture (2) is synergistic against mould *A. brasiliensis*;
mixture (3) is synergistic against gram positive bacterium *S. aureus*;
mixture (4) is synergistic against gram positive bacterium *S. aureus*;
mixture (5) is synergistic against mould *A. brasiliensis*;
mixture (6) is synergistic against gram positive bacterium *S. aureus*;
mixture (7) is synergistic against mould *A. brasiliensis*.

* * * * *